United States Patent [19]

Duncia

[11] Patent Number: 5,376,666
[45] Date of Patent: Dec. 27, 1994

[54] ANGIOTENSION-II RECEPTOR BLOCKING, AZACYCLOALKYL OR AZACYCLOALKENYL

[75] Inventor: John J. V. Duncia, Wilmington, Del.

[73] Assignee: The Du Pont Merck Pharmaceutical Company, Wilmington, Del.

[21] Appl. No.: 983,307

[22] Filed: Nov. 30, 1992

[51] Int. Cl.$^5$ .................. A61K 31/44; C07D 471/04; C07D 211/78
[52] U.S. Cl. ................ 514/303; 514/212; 514/235.8; 514/236.2; 514/326; 514/341; 514/381; 514/397; 540/603; 544/131; 546/210; 546/276; 546/278; 546/118; 548/252; 548/253; 548/254; 548/314.7
[58] Field of Search .............. 540/603; 546/210, 276, 546/278, 118; 548/252, 253, 254, 314.7; 544/131; 514/212, 235.8, 236.2, 303, 326, 341, 381, 397

[56] References Cited

U.S. PATENT DOCUMENTS 5,128,327 7/1992 Chakravarty et al. .............. 546/118
5,210,092 5/1993 Oku et al. ............................ 548/159

FOREIGN PATENT DOCUMENTS 8016391 1/1992 Australia ............................ 233/84
0400974 12/1990 European Pat. Off. .............. 471/04
465368 1/1992 European Pat. Off. .............. 233/84

*Primary Examiner*—Bernard Dentz
*Attorney, Agent, or Firm*—Norbert F. Reinert

[57] ABSTRACT

Novel heterocycle substituted azocycloalkane benzylimidazoles of Formula (I), which are useful as angiotensin-II antagonists, are disclosed:

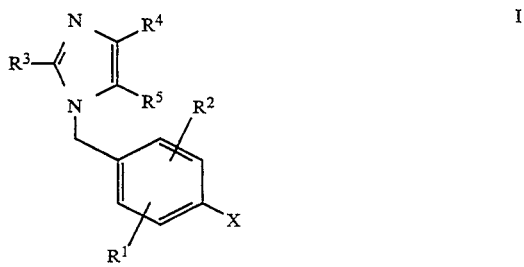

7 Claims, No Drawings

ANGIOTENSION-II RECEPTOR BLOCKING, AZACYCLOALKYL OR AZACYCLOALKENYL

FIELD OF THE INVENTION

This invention relates to azocyclalkane benzylimidazoles. The invention also relates to pharmaceutical compositions containing these imidazoles and pharmaceutical methods using them, alone and in conjugation with other drugs, especially diuretics, angiotensin converting enzyme (ACE) inhibitors, and non-steroidal anti-inflammatory drugs (NSAIDS).

BACKGROUND OF THE INVENTION

The compounds of this invention inhibit the action of the hormone angiotensin II (AII) and are useful therefore in alleviating angiotensin induced hypertension. The enzyme renin acts on a blood plasma α2-globulin, angiotensinogen, to produce angiotensin I, which is then converted by ACE to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a NSAID can prevent renal failure which sometimes results from administration of a NSAID.

Several peptide analogs of AII are known to inhibit the effects of this hormone by competitively blocking the receptors, but their experimental and clinical applications have been limited by their partial agonist activity and lack of oral absorption (M. Antonaccio, *Clin. Exp. Hypertens.*, 1982, A4, 27–46; D. H. P. Streeten and G. H. Anderson, Jr.—*Handbook of Hypertension, Clinical Pharmacology of Antihypertensive Drugs*, ed., A. E. Doyle, Vol. 5, pages 246–271, Elsevier Science Publisher, Amsterdam, The Netherlands, 1984).

Several non-peptide antagonists of angiotensin II, including some biphenylmethyl imidazoles, have been disclosed. U.S. Pat. Nos. 5,137,902 and 5,138,069 disclose biphenylmethylimidazoles (A) where $R^1$ may be a

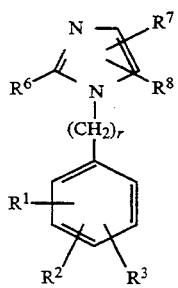

(A)

phenyl substituted in the 2'-position with acidic functional groups, such as carboxy, —$CONHSO_2R$ and tetrazole, and where $R^8$ may be formyl, acyl, carboxy, alkoxycarbonyl, aminocarbonyl, alkoxyalkyl and hydroxyalky. PCI publication WO 91-00277 and Ser. No. 07/900,540 now U.S. Pat. No. 5,254,546 disclose substituted imidazoles of the same basic structure where $R^7$ may be optionally substituted aryl or heteroaryl. European Application EP 479,479 (Merck) discloses biphenylmethyl imidazoles (B) where $R_1B$ may represent alkyl, $R^3$ may be H, alkyl, alkenyl or alkynyl, perfluoroalkyl, halogen, $NO_2$, CN or optionally substituted phenyl, $R^4$ includes formyl, acyl, carboxy, alkoxycarbonyl, aminocarbonyl, alkoxyalkyl and hydroxyalkyl, X may be a single bond, and $R^5$ includes —$SO_2NH$-heteroaryl, —$SO_2NHCOR^{12}$ and —$SO_2NH$-$CONR^2R^{12}$, in which $R^2$ is H or alkyl, and $R^{12}$ is aryl, heteroaryl, cycloalkyl, perfluoroalkyl or optionally substituted C1–C4 alkyl, where the alkyl substituents include aryl, heteroaryl, alkyl, OH, SH, alkoxy, thioalkoxy, halo, carboxy, alkoxycarbonyl, $NO_2$, optionally substituted amino and various phosphoryl radicals.

European Application Number 90305850.1 (EP 400,974) discloses imidazo-fused 6-membered heterocycles (C) as angiotensin II antagonists useful in the treatment of hypertension and congestive heart failure, where A, B, C,

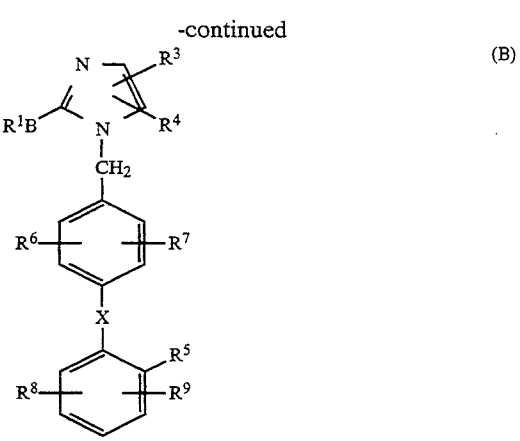

(B)

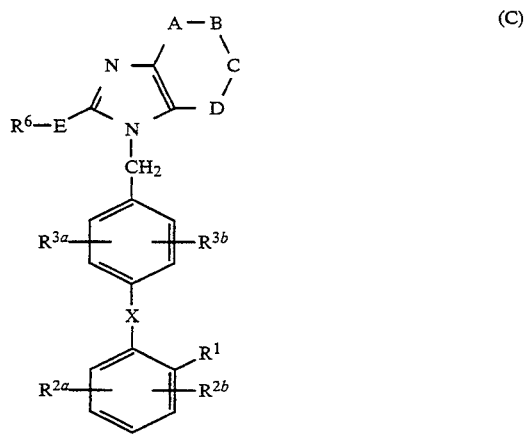

(C)

and C are independently carbon or nitrogen atoms.

Australian Application AU-A-80163/91 (EP 465,368, Roussel-Uclaf) discloses substituted imidazoles (D) where $R^1$ may be alkyl, m may be 1, either $R^2$ or $R^3$ is $OR^4$ or a sulfurous group of structure —$S(O)_nR^4$,

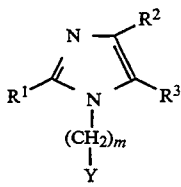

—SO(R4)=NS(O)nX' or —SSR4, where R4 represents a variety of optionally substituted alkyl, alkenyl, alkynyl, acyl or nitrogenous or sulfurous radicals. The imidazole nitrogen substituent $(CH_2)_m$-Y may represent a biphenylmethyl group, which may be substituted in the 2'-position by acidic groups, such as —$(CH_2)_{m1}$—S—$(O)_{m2}$—X— $R^{10}$, in which m1 may be 0–4, m2 may be 0–2, X may be a single bond, —NH—, —NH—CO—, or —NH—CO—NH— and $R^{10}$ is an optionally substituted alkyl, alkenyl, aryl or heteroaryl radical.

None of the references describe the compounds of this invention.

It is well known that two types of angiotensin II receptors are widely distributed in various mammalian tissues (P. C. Wong et al., *Cardiovascular Drug Reviews* 1991; 9: 317–339; *Trends in Endocrinol. Metab.* 1992; 3: 211–217). The angiotensin II receptor most directly involved in the mediation of blood pressure is termed the $AT_1$ receptor, and is characterized by high sensitivity to the non-peptide antagonist DuP 753. A second angiotensin II receptor, designated $AT_2$, is sensitive to another class of non-peptide AII antagonists, represented by PD123177 (ibid.), and CGP42112A. Angiotensin II has approximately equal affinity for both receptor subtypes.

Recent evidence suggests that the $AT_2$ receptor may have a role in mediating the synthesis and breakdown of cardiac connective tissues. For example, Matsubara et

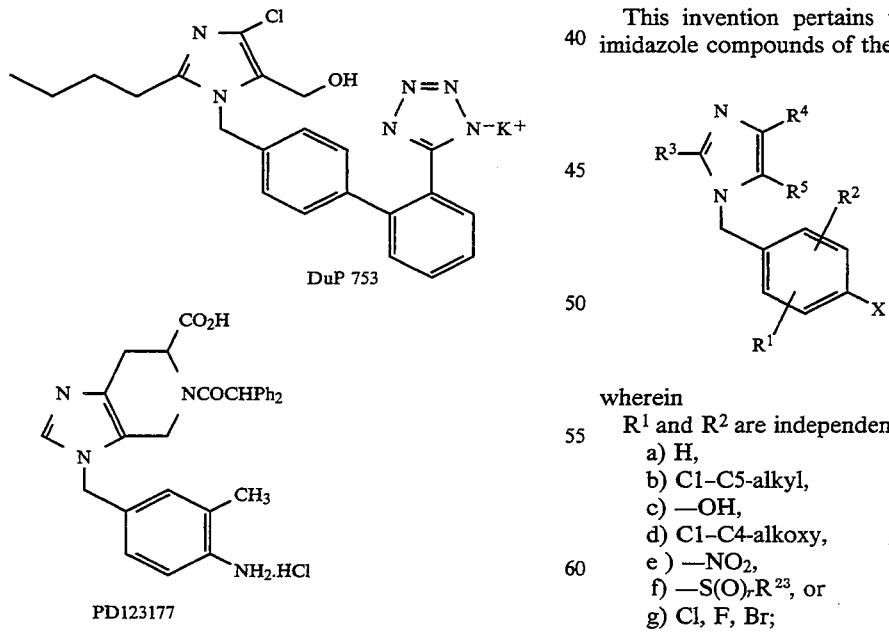

CGP42112A = nicotinic acid-Tyr—(Na-benzyloxycarbonyl-Arg)Lys—His—Pro—Ile—OH al. (*The FASEB Journal* 6, 4: A941, 1992) have reported that PD123177, but not DuP 753, blocks the AII-stimulated inhibition of collagenase in cultured cardiac fibroblasts. Both PD123177 and DuP 753 are reported by Zhou et al. to block the AII-stimulated increase in collagen synthesis in cardiac fibroblasts (*The FASEB Journal* 6, 4: A1914, 1992).

Tsutsumi and Saavedra have found $AT_2$ receptors in cerebral arteries (*Am. J. Physiol.* 261: H667–H670, 1991). An analog of PD123177, PD123319, has been reported by Brix and Haberl (*The FASEB Journal* 6, 4: A1264, 1992) to block the pial artery dilation induced by angiotensin II in a rat cranial window preparation monitored by intravital microscopy. This suggests that the $AT_2$ receptor may have a role in modifying cerebral blood flow.

The $AT_2$ selective antagonist CGP42112A has been reported by LeNoble et al. (*The FASEB Journal* 6, 4: A937, 1992) to block the increase in microvascular density induced by angiotensin II in the chick chorioallantoic membrane, suggesting that angiotensin II may in some contexts mediate angiogenesis through $AT_2$ receptors.

As noted above, DuP 753, disclosed in U.S. Pat. No. 5,138,069, is a selective $AT_1$ antagonist, having extremely low affinity for the $AT_2$ receptor. No data is presented in U.S. Pat. No. 5,138,069 or the other references above which suggests that any of the compounds disclosed possess high $AT_2$ affinity.

In addition to potent $AT_1$ antagonist and antihypertensive properties, the imidazole compounds of the present invention possess potent $AT_2$ antagonist properties. Since $AT_1$ antagonism leads to increased levels of circulating angiotensin II in vivo (Y. Christen et al., *Am. J. Hypertension,* 1991; 4: 350S–353S), and the $AT_2$-mediated consequences, if any, of higher AII levels are unknown, simultaneous $AT_1$/$AT_2$ antagonism may prove desirable during $AT_1$-targeted therapy.

SUMMARY OF THE INVENTION

This invention pertains to angiotensin-II blocking imidazole compounds of the following formula (I):

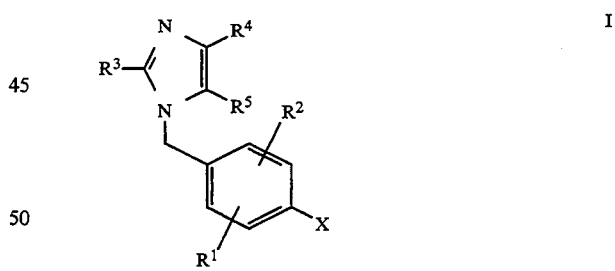

wherein
$R^1$ and $R^2$ are independently
  a) H,
  b) C1-C5-alkyl,
  c) —OH,
  d) C1-C4-alkoxy,
  e) —$NO_2$,
  f) —$S(O)_rR^{23}$, or
  g) Cl, F, Br;
$R^3$ is alkyl, alkenyl or alkynyl of 2-7 carbon atoms;
$R^4$ is
  a) H,
  b) Cl, Br, I,
  c) C1-C4-alkyl,
  d) C1-C4-perfluoroalkyl, e) phenyl or phenyl optionally substituted with halogen, C1–C4-alkyl, —OH or C1–C4-alkoxy, or f) —S(O)$_r$R$^{23}$;

R$^5$ is
 a) H,
 b) C1–C4 alkyl,
 c) —(CH$_2$)$_m$CHR$^{15}$OR$^{16}$,
 d) —COR$^{17}$,
 e) —(CH$_2$)$_m$CHR$^{15}$COR$^{17}$,
 f) —CR$^{18}$=CR$^{19}$COR$^{17}$,
 g) —CONHOR$^{20}$,
 h) —(CH$_2$)$_m$OCOR$^{16}$,
 i) —CH$_2$NHCOR$^{15}$,
 j) —(CH$_2$)$_m$NHSO$_2$R$^{23}$,
 l) tetrazol-5-yl, or
 m) —CONHSO$_2$R$^9$;

R$^4$ and R$^5$ taken together to be

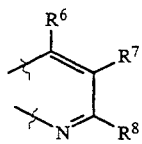

R$^6$, R$^7$, R$^8$ are independently
 a) H,
 b) C1–C4-alkyl, either unsubstituted or substituted with:
  i) —OH,
  ii) —CO$_2$R$^{32}$,
  iii) —NH$_2$,
  iv) (C1–C4-alkyl)amino,
  v) di(C1–C4-alkyl)amino,
 c) halo,
 d) —CF$_3$,
 e) —OH,
 f) —N(R$^{32}$)$_2$,
 g) C1–C4-alkoxy,
 h) —CO$_2$R$^{32}$,
 i) —CONH$_2$,
 j) —C3–C7-cycloalkyl,
 k) aryl, wherein aryl is phenyl or napthyl optionally substituted with one or two substituents selected from the group consisting of halo (F, Cl, Br, I), C1–C4-alkyl, C1–C4-alkoxy, —NO$_2$, —CF$_3$, C1–C4-S(O)$_r$—, —OH, —NH$_2$, —NH(C1–C4-alkyl), —N(C1–C4-alkyl)$_2$, —CO$_2$R$^{10}$;
 l) heterocyclic, wherein heterocyclic is a five- or six-membered saturated or unsaturted ring containing 1–3 three heteroatoms selected from the group consisting of O, N or S wherein S may be in the form of sulfoxide or sulfone and which may be optionally substituted with one or two substituents which are members selected from the group consisting of halo (F, Cl, Br, I), C1–C4-alkyl, C1–C4-alkoxy, —NO$_2$, —CF$_3$, C1–C4-S(O)$_r$—, —OH, —NH$_2$, —NH(C1–C4-alkyl), —N(C1–C4-alkyl)$_2$, —CO$_2$R$^{10}$;
 m) —CONHSO$_2$R$^9$, or
 n) tetrazol-5-yl;

R$^9$ is
 a) C1–C4-alkyl,
 b) phenyl or phenyl optionally substituted with halogen, C1–C4-alkyl, —OH or C1–C4-alkoxy;

R$^{10}$ is H, C1–C4-alkyl or benzyl;

X is saturated or unsaturated

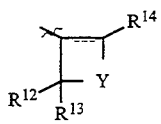

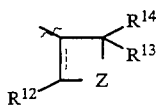

Y is
 a) —NR$^{11}$(CR$^{25}$R$^{26}$)—,
 b) —NR$^{11}$(CR$^{25}$R$^{26}$)(CR$^{27}$R$^{28}$)—,
 c) —(CR$^{25}$R$^{26}$)NR$^{11}$(CR$^{27}$R$^{28}$)—,
 d) —NR$^{11}$(CR$^{25}$R$^{26}$)(CR$^{27}$R$^{28}$)(CR$^{29}$R$^{30}$)—,
 e) —(CR$^{25}$R$^{26}$)NR$^{11}$(CR$^{27}$R$^{28}$)(CR$^{29}$R$^{30}$)—,
 f) —(CR$^{25}$R$^{26}$)(CR$^{27}$R$^{28}$)NR$^{11}$(CR$^{29}$R$^{30}$)—;

Z is
 a) —(CR$^{25}$R$^{26}$)NR$^{11}$—,
 b) —(CR$^{25}$R$^{26}$)(CR$^{27}$R$^{28}$)NR$^{11}$—,
 c) —(CR$^{25}$R$^{26}$)NR$^{11}$(CR$^{27}$R$^{28}$)—,
 d) —(CR$^{25}$R$^{26}$)(CR$^{27}$R$^{28}$)(CR$^{29}$R$^{30}$)NR$^{11}$—,
 e) —(CR$^{25}$R$^{26}$)NR$^{11}$(CR$^{27}$R$^{28}$)(CR$^{29}$R$^{30}$)—,
 f) —(CR$^{25}$R$^{26}$)(CR$^{27}$R$^{28}$)NR$^{11}$(CR$^{29}$R$^{30}$)—;

R$^{11}$ is
 a) —COR$^{31}$,
 b) —CO$_2$R$^{31}$,
 c) —CONHR$^{31}$,
 d) —CONR$^{31}$R$^{27}$,
 e) —(CH$_2$)$_p$CHR$^{31}$R$^{27}$,
 f) —SO$_2$R$^{31}$;

R$^{12}$, R$^{13}$ are independently
 a) H,
 b) alkyl of 1–7 carbon atoms, or
 c) phenyl or phenyl optionally substituted with one or two substituents selected from the group consisting of halo (F, Cl, Br, I), C1–C4-alkyl, C1–C4-alkoxy, —NO$_2$, —CF$_3$, C1–C4-S(O)$_r$—, —OH, —NH$_2$, —NH(C1–C4-alkyl), —N(C1–C4-alkyl)$_2$, —CO$_2$R$^{10}$;

R$^{14}$ is
 a) —CO$_2$H,
 b) —SO$_2$NHCO$_2$R$^{24}$,
 c) —SO$_2$NHCOR$^{24}$,
 d) —CONHSO$_2$R$^{24}$,
 e) —SO$_2$NHCONHR$^{24}$, or
 f) —SO$_2$NHCSNHR$^{24}$, or

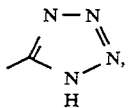

R$^{15}$ is
 a) C$_1$–C$_4$-alkyl,
 b) C$_3$–C$_6$-cycloalkyl,
 c) aryl as defined above, or
 d) —(C$_1$–C$_4$-alky)-aryl, —(C$_1$–C$_4$-alkyl)-aryl, where aryl is as defined above,
 e) H;

R$^{16}$ is
 a) H,
 b) C$_1$–C$_6$-alkyl,
 c) aryl as defined above, d) —(CH$_2$)$_p$(aryl), where aryl is as defined above, or
e) —(CH$_2$)$_p$CH(diaryl), where aryl is as defined above;

R$^{17}$ is
a) H,
b) —OR$^{16}$,
c) —NR$^{21}$R$^{22}$;

R$^{18}$ and R$^{19}$ are independently
a) H,
b) C$_1$–C$_4$-alkyl,
c) aryl as defined above,
d) —CH$_2$aryl, where aryl is as defined above;

R$^{20}$ is
a) H,
b) methyl,
c) benzyl;

R$^{21}$ and R$^{22}$ are independently
a) H,
b) C$_1$–C$_4$-alkyl,
c) aryl as defined above,
d) —CH$_2$aryl, where aryl is as defined above, or taken together comprise
e) —(CH$_2$)$_u$—, where u is 2 to 5,
f) a morpholine ring;

R$^{23}$ is
a) —CF$_3$,
b) C1–C6-alkyl,
c) phenyl;

R$^{24}$ is
a) aryl as defined above,
b) C3–C7-cycloalkyl,
c) C1–C4-perfluoroalkyl,
d) C1–C10-alkyl optionally substituted with a substituent selected from the group consisting of:
  i) aryl as defined above,
  ii) heteroaryl, wherein heteroaryl is an unsubstituted, monosubstituted or disubstituted 5- or 6-membered aromatic ring which can optionally contain from 1 to 3 heteroatoms selected from the group consisting of O, N, and S and wherein the substituents are members selected from the group consisting of —OH, —SH, C$_1$–C$_4$-alkyl, C$_1$–C$_4$-alkoxy, —CF$_3$, halo, —NO$_2$, —CO$_2$R$^{10}$, —NH$_2$, C$_1$–C$_4$-alkylamino, C$_1$–C$_4$-dialkylamino,
  iii) —OH, —SH, C$_1$–C$_4$-alkyl, C$_1$–C$_4$-alkoxy, C$_1$–C$_4$ alkylthio, —CF$_3$, halo, —NO$_2$, —CO$_2$R$^{10}$, —NH$_2$, C$_1$–C$_4$-alkylamino, C$_1$–C$_4$-dialkylamino, —PO$_3$H$_2$;
e) heteroaryl as defined above;

R$^{25}$, R$^{26}$, R$^{27}$, R$^{28}$, R$^{29}$, R$^{30}$ are independently
a) H,
b) C1–C7-alkyl,
c) phenyl or phenyl optionally substituted with one or two substituents selected from the group consisting of halo (F, Cl, Br, I), C1–C4-alkyl, C1–C4-alkoxy, —NO$_2$, —CF$_3$, C1–C4-S(O)$_r$, —OH, —NH$_2$, —NH(C1–C4-alkyl), —N(-C1–C4-alkyl)$_2$, —CO$_2$R$^{10}$,
d) C3–C7-cycloalkyl;

R$^{31}$ is
a) —CH$_3$,
b) —CH$_2$CH$_3$,
c) —CH$_2$CH$_2$CH$_3$,
b) C4–C15-alkyl,
c) aryl as defined above, d) —(C1–C10-alkyl)-aryl, where aryl is as defined above,
e) —(CH$_2$)$_p$CH(diaryl), where aryl is as defined above
f) C3–C7-cycloalkyl,
g) —C1–C5-alkyl-(C3–C7-cycloalkyl),
h) —(CH$_2$)$_p$CH(C3–C7-cycloalkyl)(aryl), where aryl is as defined above,
i) —(CH$_2$)$_p$CH(C1–C6-alkyl)(aryl), where aryl is defined as above;

R$^{32}$ is
a) C1–C15 alkyl,
b) aryl defined as above, or
c) aryl (C1–C10)alkyl, where aryl is defined as above;

m is 0 to 2;
p is 0 to 6;
r is 0 to 2;
u is 2 to 5; and pharmaceutically acceptable salts thereof.

Preferred are compounds of Forumla I wherein:
R$^1$ and R$^2$ are independently
a) H,
b) C1–C5-alkyl,
g) Cl, F, Br;

R$^3$ is alkyl or alkenyl of 2–7 carbon atoms;

R$^4$ is
a) Cl, Br, I,
b) C1–C4-alkyl,
c) C1–C4-perfluoroalkyl,
d) phenyl or phenyl optionally substituted with halogen, C1–C4-alkyl, —OH or C1–C4-alkoxy;

R$^5$ is
a) —(CH$_2$)$_m$CHR$^{15}$OR$^{16}$,
b) —COR$^{17}$,
c) —(CH$_2$)$_m$CHR$^{15}$COR$^{17}$,
d) —CR$^{18}$=CR$^{19}$COR$^{17}$,
e) —CONHOR$^{20}$,
f) —(CH$_2$)$_m$NHSO$_2$R$^{23}$,
g) —CONHSO$_2$R$^9$;

R$^6$, R$^7$, R$^8$ are independently
a) H,
b) C1–C4-alkyl
c) —CO$_2$R$^{32}$,
d) —CONHSO$_2$R$^9$, or
e) phenyl;

R12, R13 are independently
a) H,
b) C1–C7-alkyl, or
c) phenyl;

R$^{24}$ is
a) aryl as defined above,
b) C3–C7-cycloalkyl,
c) C1–C4-perfluoroalkyl,
d) C1–C10-alkyl optionally substituted with phenyl.

More preferred are the preferred compounds of Forumla I wherein:
R$^5$ is
a) —CH$_2$OR$^{16}$,
b) —COR$^{17}$,
c) —CONHSO$_2$R$^9$;

R$^6$, R$^7$, R$^8$ are independently
a) H,
b) C1–C4-alkyl
c) —CO$_2$R$^{32}$,
d) —CONHSO$_2$R$^9$;

Y is a) —NR$^{11}$(CR$^{25}$R$^{26}$)—,
b) —NR$^{11}$(CR$^{25}$R$^{26}$)(CR$^{27}$R$^{28}$)—,
c) —(CR$^{25}$R$^{26}$)NR$^{11}$(CR$^{27}$R$^{28}$)—;

Z is
a) —(CR$^{25}$R$^{26}$)NR$^{11}$—,
b) —(CR$^{25}$R$^{26}$)(CR$^{27}$R$^{28}$)NR$^{11}$—,
c) —(CR$^{25}$R$^{26}$)NR$^{11}$(CR$^{27}$R$^{28}$)—.

Specifically preferred compounds include:
1-Diphenylacetyl-4-[4-(5,7-dimethyl-2-ethylimidazopyridin-3-yl)methyl)phenyl]-3-tetrazol-5-yl)-1,2,3,6-tetrahydropyridine
1-Diphenylacetyl-4-[4-(5,7-dimethyl-2-ethylimidazopyridin-3-yl)methyl)phenyl]-3-(n-butylsulfonamidocarbonyl)-1,2,3,6-tetrahydropyridine
1-Diphenylacetyl-4-[4-(5,7-dimethyl-2-ethylimidazopyridin-3-yl)methyl)phenyl]-3-carboxy-1,2,3,6-tetrahydropyridine Note that throughout the text when an alkyl substituent is mentioned, the normal alkyl structure is meant (e.g. butyl is n-butyl) unless otherwise specified. However, in the definition of radicals above (e.g. R$^3$), both branched and straight chains are included in the scope of alkyl, alkenyl and alkynyl.

It should be noted in the foregoing structural formula, when a radical can be a substituent in more than one previously defined radical, that first radical can be selected independently in each previously defined radical. For example, R$^1$ can be —SO$_2$R$^{23}$ and R$^5$ can be —CH$_2$NHSO$_2$R$^{23}$. R$^{23}$ need not be the same substituent in each of R$^1$ and R$^5$, but can be selected independently for each of them.

It is understood that many of the compounds of the present invention contain one or more chiral centers and that these stereoisomers may possess distinct physical and biological properties. The present invention comprises all of the stereoisomers or mixtures thereof.

If the pure enantiomers or diastereomers are desired, they may be prepared using starting materials with the appropriate stereochemistry, or may be separated from mixtures of undesired stereoisomers by standard techniques, including chiral chromatography and recrystallization of diastereomeric salts.

Pharmaceutically acceptable salts include both the metallic (inorganic) salts and organic salts; a nonexhaustive list of which is given in *Remington's Pharmaceutical Sciences* 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a novel compound of Formula (I), and methods of using the novel compounds of Formula (I) to treat hypertension and congestive heart failure. The pharmaceutical compositions can optionally contain one or more other therapeutic agents, such as a diuretic, an angiotensin I converting enzyme (ACE) inhibitor or a non-steroidal antiinflammatory drug (NSAID). Also within the scope of this invention is a method of preventing renal failure resulting from administration of a NSAID which comprises administering a novel compound of Formula (I) in stepwise or physical combination with the NSAID. The compounds of this invention can also be used as diagnostic agents to test the renin angiotensin system.

DETAILED DESCRIPTION OF THE INVENTION

The novel compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgement as to the order of synthetic steps, protecting groups required, deprotection conditions, and activation of a benzylic position to enable attachment to nitrogen on the imidazole nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

The compounds (I) described in the scope of this application can be made by alkylation of an imidazole derivative (1) with a suitably elaborated benzyl halide, tosylate, or mesylate (2) (X=Cl, Br, I, OSO$_2$R where R=CH$_3$, Tol, etc.) in a solvent such as DMF, THF, or DMSO in the presence of an acid scavenger such as sodium or potassium carbonate, sodium or potassium bicarbonate, Huenig's base, or collidine at room temperature to the reflux temperature of the solvent to yield benzylimidazole (3) (Scheme 1). Another method entails deprotonation of the imidazole (1) with a base followed by alkylation with benzyl halide, tosylate, mesylate (2) in solvents and temperatures as described above. Bases include sodium or potassium hydride, lithium diisopropylamide (LDA), sodium methoxide, potassium t-butoxide, etc. In Scheme 1, the benzyl-X moiety (2) is substituted with an azocyclohexene ring. It should be understood by the reader that the nitrogen ring isomer depicted here and in subsequent schemes may be replaced by other isomers listed in the scope of this application. In addition, the azocyclohexene ring depicted here and in subsequent schemes may be replaced with an azocyclopentene or azocycloheptene ring system. Both the 5- and 7-membered ring systems may also undergo the same transformations as does the azocyclohexene ring system which will be the only ring system that will formally be depicted and discussed in the subsequent disclosure. In addition, in compound (2), one may replace the BOC group with an R$^{11}$ group if the R$^{11}$ group is compatible with the alkylation reaction conditions, many of which in the scope are.

The BOC group of benzylimidazole (3) may be deprotected with excess trifluoroacetic acid in an inert solvent such as THF with or without anisole as a t-butyl cation scavenger. Water may also be added to scavenge t-butyl cations. The reaction is run at 0° C. to room temperature. Trimethylsilyl iodide may also be used in an inert solvent to deprotect a BOC group (T. Tsuji, et al. Tet. Lett. 2793 (1979).

The nitrogen in the azocycloalkene portion may be protected by other compatible groups besides a BOC group such as CBZ, THP, MEM, MOM, etc., as found in T. W. Greene "Protective Groups in Organic Chemistry" (New York, 1981) Wiley-Interscience.

Amine (4) may be acylated with an acid chloride, i.e. diphenylacetyl chloride, to yield compound (5) or in general $R^{11}=COR^{31}$. This is done either under Schotten-Baumann conditions (E. Baumman, Ber. Deut. Chem. Ges. 19, 3218 (1886)) using aqueous base or by simply stirring the acid chloride and amine in an inert solvent such as methylene chloride or THF in the presence of an acid scavenger, examples of which are listed above, at 0° C. to room temperature. The acid chloride may also be replaced by a chloroformate to yield a carbamate ($R^{11}=CO_2R^{31}$) and by a sulfonyl chloride ($R^{11}=SO_2R^{31}$) under similar reaction conditions. Alternatively, amine (4) may be reacted with a carboxylic acid in the presence of a coupling agent such as DCC or carbonyldiimidazole (CDI) to yield amide (5) or $R^{11}=COR^{31}$ in general. Likewise, amine (4) may be first reacted with CDI followed by reaction with a primary amine to yield $R^{11}=CONHR^{31}$ or with a secondary amine to yield $R^{11}=CONR^{31}R^{31}$. Alternatively, reaction of amine (4) with isocyanate $R^{31}N=C=O$ in an inert solvent such as THF at 0° C. to reflux with or without DMAP (4-N,N-dimethylaminopyridine) catalyst yields $R^{11}=CONHR^{31}$. Finally, alkylation of the amine nitrogen in (4) with an alkyl halide in an inert solvent such as DMSO, DMF, or THF with or without an acid scavenger as described previously yields $R^{11}=(CH_2)_nCHR^{31}R^{27}$. This alkylation may be performed using an alkyl halide, tosylate, mesylate or triflate at $-78°$ C. to room temperature and even sometimes at reflux temperatures.

The ester group in (5) is then saponified to the carboxylic acid by procedures familiar to one skilled in the art. For example, compound (5) may be stirred in THF or methanol in the presence of 1 to 20 equivalents of aqueous 1-10N NaOH or KOH at room temperature to the reflux temperature of the solvent. It is at this step that some double bond migration may occur in the azoalkene ring to yield products in which the double bond is not conjugated with the carboxylic acid. One may obtain pure conjugated product, unconjugated product, or a mixture of both.

The carboxylic acid (6) may be subsequently reacted with CDI in an inert solvent at room temperature to the reflux temperature of the solvent followed by reaction with a sulfonamide in the presence of a non-nucleophilic base such as DBU (1,8-diazabicyclo[5.4.0]undec-7-ene) at room temperature to the reflux temperature of the solvent to yield acylsulfonamide (7).

It should be understood that all of the above transformations in going from compound (5) to (7) can be performed in the presence of all of the different $R^{11}$ groups mentioned in the scope and for all of the different azocycloalkene ring systems also mentioned in the scope of this application. Only the one azocyclohexene system is shown in Scheme 1 and in all subsequent schemes in order to make it easier for the reader to follow the sequence of organic transformations. In addition, it should be understood by the reader that all of the azocycloalkene rings shown may be substituted with $R^{25}$—groups as stipulated in the scope of this application. This is also true for all of the azocycloalkenes depicted in the subsequent schemes where applicable. The same is true for substitution on the benzyl aromatic ring by $R^1$ and $R^2$. They have been omitted in many of the schemes for the sake of clarity.

The azocycloalkene system may be hydrogenated to yield the fully saturated system in inert solvents such as THF or methanol using catalysts such as 5–10% Pd on carbon or platinum oxide, a procedure familiar to one skilled in the art. The double bond may also be reduced by dissolving metal-type reductions or homogeneous reducing agents such as Mg: T. Hudlicky, G. Sinai-Zingde, M. G. Natchus, Tet. Lett., 28, 5287 (1987); $SnCl_2$: H. Rakoff, B. H. Miles, J. Org. Chem., 26, 2581 (1961); Zn/HOAc: D. J. Goldsmith, C. Kwong, G. Srousi, J. Org. Chem., 43, 3182 (1978); RED-Al, CuBr: M. F. Semmelhack, R. D. Stauffer, J. Org. Chem., 40, 3619(1975).

The imidazole portion (1) may be synthesized as described in U.S. Pat. Nos. 5,137,902 and 5,138,069 as well as Australian Patent application number AU-A-80163/91 (published on Sep. 1, 1992). If there is an additional pyridyl ring fused onto the imidazole portion, then the imidazopyridine can be synthesized by the procedures disclosed in European Patent Application number 400974 (May 30, 1990).

The synthesis of the bottom portion of the molecules described in this application, namely the benzyl portion (2), is shown in Scheme 2.

Scheme 1

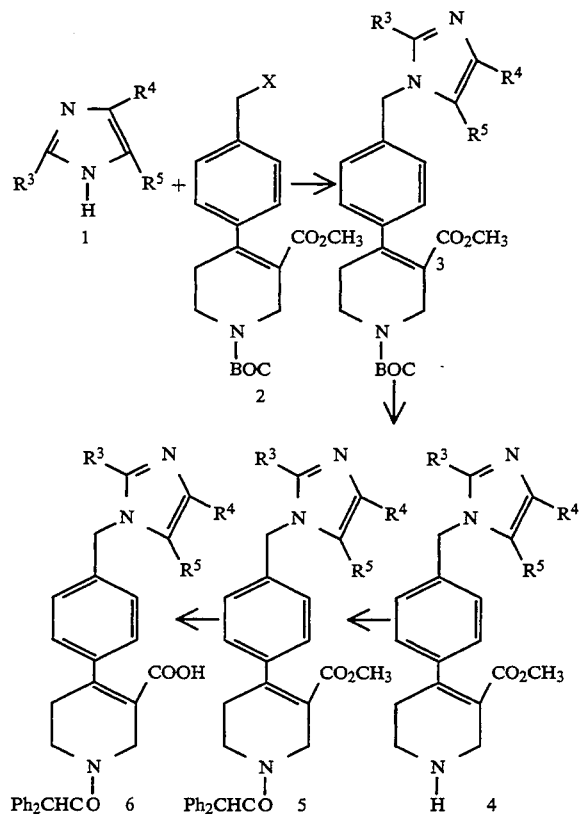

-continued
Scheme 1

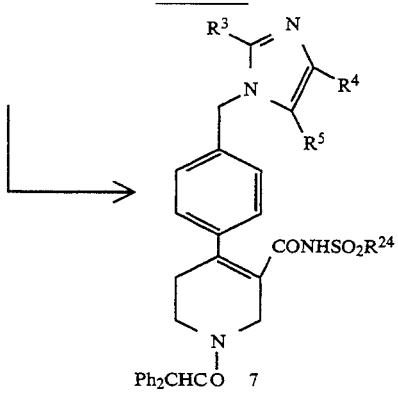

Scheme 2

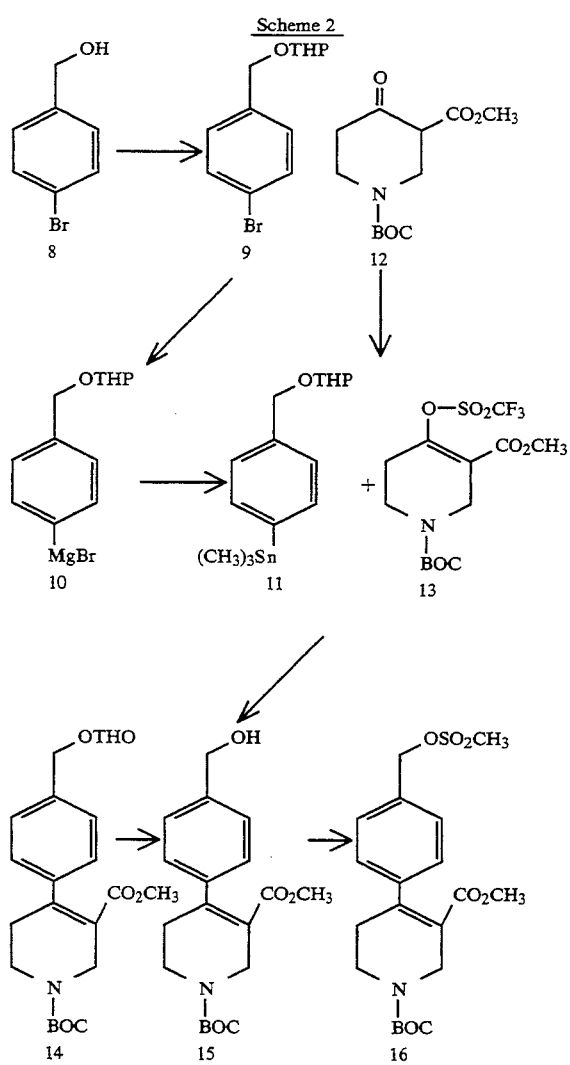

Benzyl alcohol (8) is first protected with a THP group (Scheme 2) in an inert solvent such as ether or THF using dihydropyran and a catalytic amount of acid (TsOH, POCl₃, etc. ) at room temperature or heat if necessary to yield (9). The alcohol (8) may also be protected with a variety of other protecting groups compatable with the subsequent Grignard or metallation chemistry. These groups include MEM, MOM, TBDMS, methyl ether, etc. (see T. W. Greene "Protective Groups in Organic Chemistry" (New York, 1981) Wiley-Interscience, pp. 10–50) and which are familiar to one skilled in the art. The halogen (bromine, for example, in Scheme 2) is reacted with magnesium to form the Grignard reagent (10) by procedures familiar to one skilled in the art. The MgBr can also be replaced by other metals such as lithium. For example, addition of n- or sec-butyllithium to (9) in THF at −78° C. or thereabouts will yield the corresponding halogen-lithium exchange product (10) where MgBr is replaced by Li. The organometallic reagent (10) (RMgBr or RLi) is then reacted with trimethylstannyl chloride in an inert solvent such as ether, THF, or dioxane at 0° C. to room temperature to yield stannane (11). Stannane (11) is then coupled to triflate (13) using a palladium catalyst (either Pd (0) or Pd(II)) in what is called the "Stille Reaction" (J. K. Stille and W. J. Scott, J. Am. Chem. Soc. 108, 3033 (1986); A. M. Echavarren and J. K. Stille, J. Am. Chem. Soc. 109, 5478 (1987); I. N. Houpis, Tet. Lett. 32, 6675 (1991)). For example, compounds (11) and (13) together with a catalytic quantity of tetrakis(triphenylphosphine)palladium (0) and lithium chloride are mixed and refluxed in an inert solvent such as THF to yield coupled product (14). Deprotection of the alcohol (with a THP group, for example, refluxing in methanol with a catalytic amount of TsOH) yields (15). Alcohol (15) (in Scheme 1, it would be compound (2) with X=OH) can be alkylated directly onto imidazole (1) using the Mitsunobu reaction (O. Mitsunobu, Synthesis, 1 (1981)) to yield (3). Or preferably, the alcohol is converted to a leaving group such as a mesylate or a tosylate, the procedure of which is familiar to one skilled in the art, and then alkylated with imidazole (1) in Scheme 1 to yield benzylimidazole (3). In addition, in compound (12), the BOC group may be replaced with R¹¹ groups, many of which are compatible with the subsequent transformations.

Enol triflate (13) in Scheme 2 is synthesized by reacting N-BOC-3-carboethoxy-4-piperidone with triflic anhydride in the presence of a base such as triethylamine in an inert solvent such as ether or methylene chloride at −78° C. to room temperature. Alternatively, the piperidone (12) can be deprotonated with sodium hydride in ether or THF at 0° C. and reacted with triflic anhydride.

Scheme 3

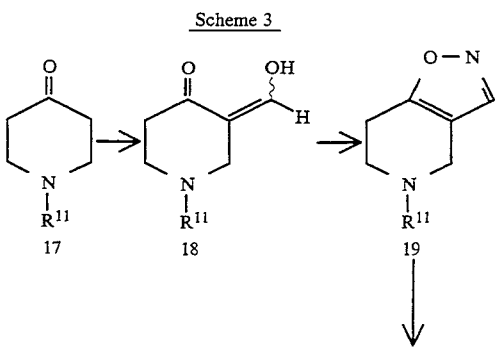

-continued
Scheme 3

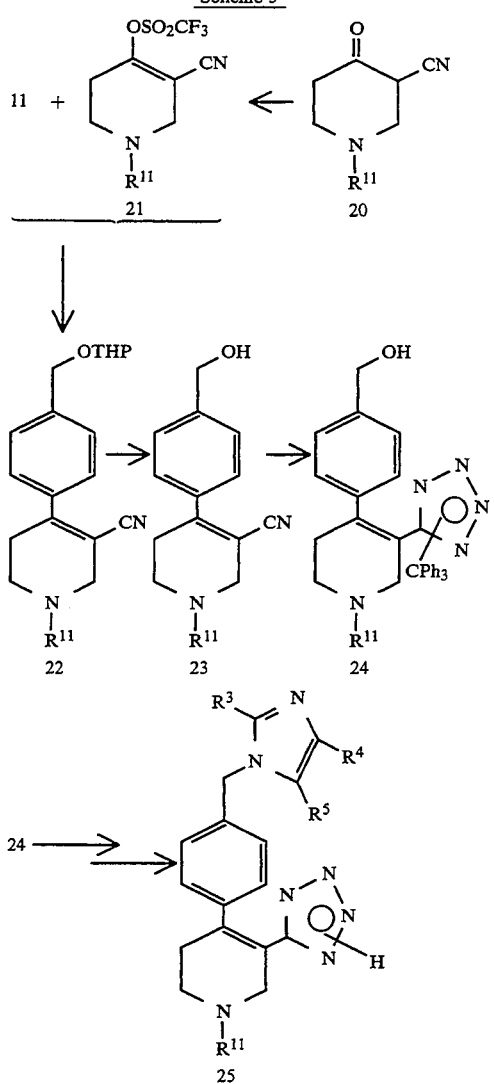

Compounds where $R^{14}$ is tetrazole may be synthesized after the method reported by W. L. Meyer, R. W. Huffman, and P. G. Schroeder, Tetrahedron, 24, 5959 (1968) as shown in Scheme 3. Piperidone (17) where $R^{11}$ is either as described in the scope or a protecting group such as BOC may be formylated with ethyl formate in the presence of a base such as sodium methoxide in an inert solvent such as benzene or toluene at 0° C. to room temperature to yield (18). Reaction with hydroxylamine in acetic acid or an inert solvent at room temperature to reflux yields isoxazole (19). Subsequent stirring in the presence of a base such as sodium ethoxide in ethanol at room temperature to reflux yields nitrile (20). Formation of the corresponding enol triflate as described previously yields (21). Stille coupling as also described previously with stannane (II) yields nitrile (22). Deprotection as described previously yields alcohol-nitrile (23). Conversion of the nitrile to the tetrazole may be achieved by reaction with a trialkyltin azide such as trimethyltin azide in an inert solvent such as toluene or xylenes at reflux. Exchange of the trialkyltin moiety for a trityl group may be accomplished by adding a base to the same reaction vessel. Bases include aqueous hydroxide or pyridine at room temperature. This is followed by the addition of trityl bromide or chloride at room temperature to yield trityl-protected tetrazole (24). Mesylation or tosylation, followed by alkylation as described previously yields (25) where the tetrazole is protected with a trityl group. Detritylation in aqeous acid with an inert organic cosolvent such as THF at room temperature or in TFA or in refluxing methanol yields free tetrazole (25). A summary of this kind of tetrazole synthesis is found in J. V. Duncia, et al., J. Org. Chem., 56, 2395 (1991).

Alternatively, nitrile (20) may be synthesized by making the enolate of (17) followed by quenching with tosylcyanide (D, Kahne, D. B. Collum, Tet. Lett., 22, 5011 (1981).

In Scheme 4, the synthesis of $R^{14}$=—$SO_2NHCOR^{24}$, —$SO_2NHCO_2R^{24}$, and —$SO_2NHCONHR^{24}$, is shown. A cyclic azoketone such as (26) where nitrogen is substitued by either a protecting group or $R^{11}$ may be alpha-brominated as shown, by first forming the silyl enol ether (27) followed by reaction with bromine to yield (28) (R. H. Reuss and A. Hassner J. Org. Chem., 39, 1785 (1974)). Displacement of the halogen with thiourea forms the isothiouronium salt (29) (E, Brand and F. C. Brand, Org. Syn. 22, 59 (1942)). Reaction of (29) with chlorine or bromine in aqueous solutions of the thiouronium salt affords sulfonyl chlorides (30) or bromides, respectively (C. Ziegler and J. M. Sprague, J. Rog. Chem. 16, 621 (1951); T. B. Johnson, J. M. Sprague J. Am. Chem. Soc. 58, 1348 (1936); 59, 1837, 2439 (1937); 61, 176 (1939)). Further reaction with a protected form of ammonia, such as bis(3,4-dimethoxybenzyl)amine yields sulfonamide (31). This reaction can be run either under Schotten-Baumann conditions described previously or by simply mixing the amine with the sulfonyl chloride in an inert solvent such as THF, with or without the presence of an acid scavenger such as potassium carbonate. If excess amine is used, the acid scavenger is unnecessary.

Protected sulfonamide (31) may be converted into the enol triflate (32) and coupled to yield azocycloalkene (33) under conditions previously described. Deprotection of the alcohol and alkylation unto imidazole derivative (1) yields sulfonamide (34). Acid cleavage of the benzyl groups (M. I. Jones, C. Froussios, D. A. Evans J. Chem. Soc. Chem. Comm. 472, (1976)) yields deprotected sulfonamide (35). Reaction of (35) with the imidazolide of carboxylic acid $R^{24}COOH$ (imidazolide is formed by reaction of the carboxylic acid with CDI) in an inert solvent such as THF or DMF at room temperature up to refluxing temperatures with or without the presence of DBU yields acylsulfonamide (36). Reaction of (35) with a chloroformate ($R^{24}OCOCl$) in an inert solvent such as THF in the presence of an acid scavenger such as pyridine with or without activation with DMAP (N,N-dimethylaminopyridine) yields sulfonylcarbamate (37). This reaction can also be run in neat pyridine as solvent. Reaction of (35) with an isocyanate or an isothiocyanate in an inert solvent such as THF yields (38) where $R^{14}$=—$SO_2NHCONHR^{24}$ or —$SO_2NHCSNHR^{24}$, respectively.

Scheme 4

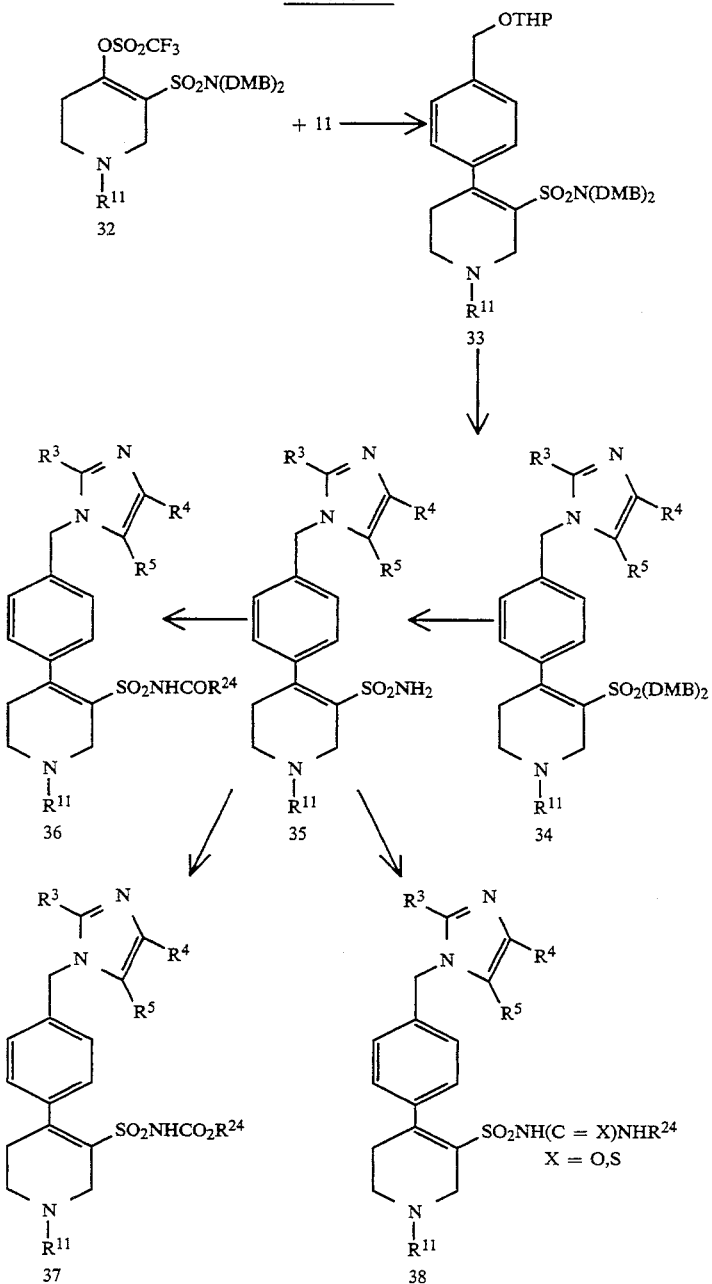

The azocycloalkanone starting materials may be synthesized by a variety of routes (many are commercially available). The most widely used route involves the Dieckmann cyclization. For example, 3 piperidones may be cyclized regioselectively when the cyclization is carried out on an unsymmetrical diester, since the acidity of the two alpha-methylene groups and the stability of the two cyclized products are different (S. M. McElvain and J. F. Vozza, J. Am. Chem. Soc. 71, 896 (1949); Z. Ozdowska, Rocz. Chem. 49, 1025 (1975); B. M. Iselin and K. Hoffmann, Helv. Chim. Acta, 37, 178 (1954); F. E. King, T. J. King, A. J. Warwich, J. Chem. Soc., 3590 (1950); H. C. Beyerman and P. Boeke, Rec. Trav. Chim. Pay-Bas, 78, 648 (1959); M. E. Freed and A. R. Day, J. Org. Chem. 25, 2105 (1960); M. E. Garst, J. N. Bonfiglio, D. A. Grudowski, J. Marks, J. Org. Chem., 45, 2307 (1980); H. Plieninger and S. Leonhauser, Chem. Ber., 92, 1579 (1959); S. M. McElvain and P. M. Laughton, J. Am. Chem. Soc., 73, 448 (1951)):

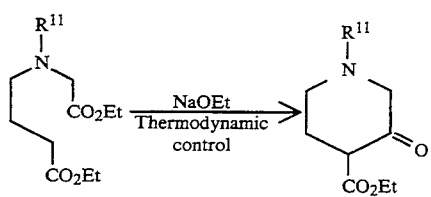

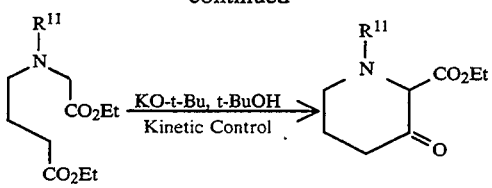

In a similar fashion, the Dieckmann cyclization may be used to make the 4-piperidones as shown below (G. Stork and S. M. McElvain, J. Am. Chem. Soc., 68, 1053 (1946); S. M. McElvain and K. Rorig, J. Am. Chem. Soc., 70, 1820 (1948); S. M. McElvain and R. E. McMahon, J. Am. Chem. Soc., 71, 901 (1949); U. M. Teotino, J. Org. Chem., 27, 1906 (1962)):

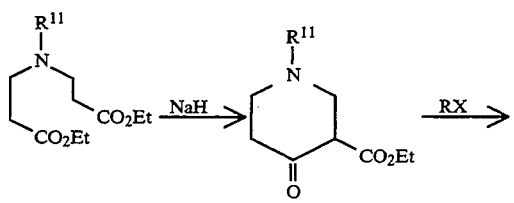

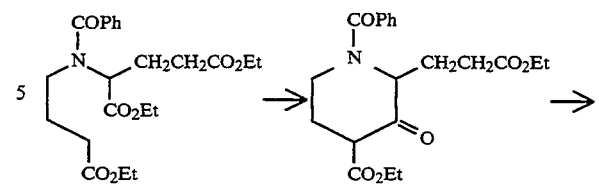

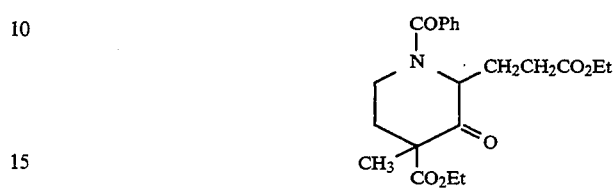

Bromides may cyclize to the corresponding azocycloalkanone (G. T. Katvalvan, N. A. Semenova, and E. A. Mistryukov, Isv. Akad. Nauk SSSR, Ser. Khim., 8, 1806 (1976) (Chem. Abstr. 85: 192510r)). This azocycloalkanone can in turn be deprotonated either under kinetic or thermodynamic conditions using bases such as LDA, K-t-OBu, NaH, etc. Depending on which enolate is formed, quenching with methyl chloroformate can yield two possible beta-ketoesters:

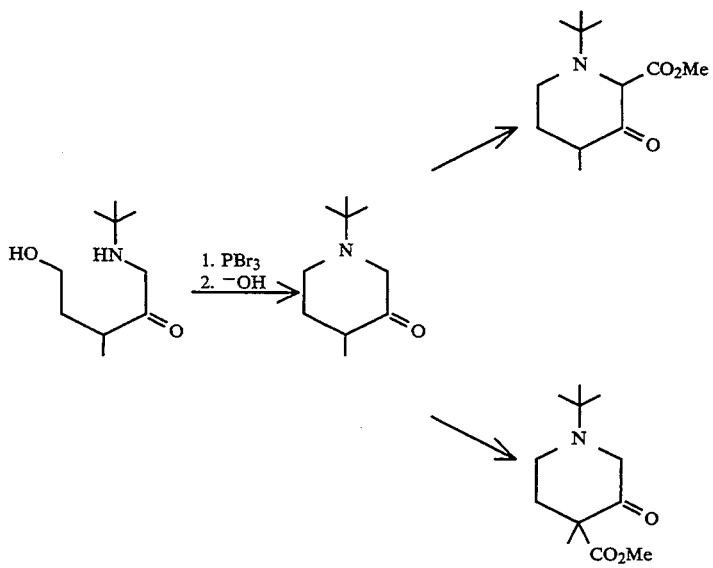

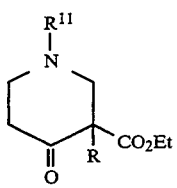

Another example of alpha-alkylation is shown as follows (N. J. Leonard, and W. V. Ruyle, J. Am. Chem. Soc., 71, 3094 (1949); J. Bosch and J. Bonjoch, J. Org. Chem., 46, 1538 (1981):

Three-component condensations of amines (or ammonia), carbonyl compounds, and active methylene compounds yield piperidones (C. R. Noller and V. Baliah, J. Am. Chem. Soc. 70, 3853 (1948); E. A. Mailey and A. R. Day, J. Org. Chem., 22, 1061 (1957); R. E. Lyle and G. G. Lyle, J. Org. Chem., 24, 1679 (1959); M. Balasubramanian and N. Padma, Tetrahedron 19, 2135 (1963); K. Bodendorf and J. Loetzbeyer, Chem. Ber., 99, 801 (1966)). Subsequent reaction with chloroformates will yield the beta-ketoester as described previously:

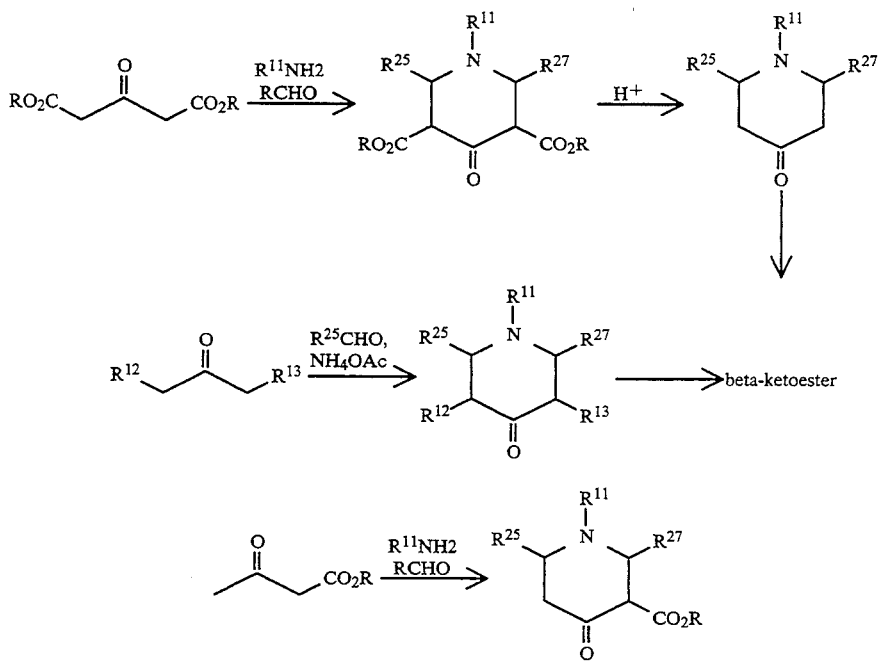

Intramolecular Mannich-type cyclization of aminoketones with carbonyl compounds yields the corresponding azocycloalkanones (M. Balasuamanian and N. Padma, Tetrahedron 19, 2135 (963); E. Matter, Helv. Chim. Acta. 31, 612 (1948) which can be subsequently derivatized as shown before to the bete-ketoesters:

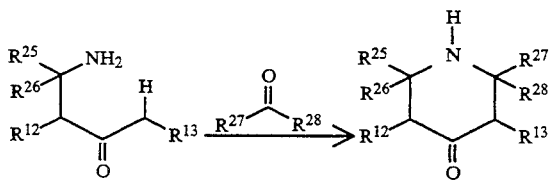

Other applicable syntheses of the azocycloalkanones may be found in M. Rubiralta, E. Giralt, A. Diez "Piperidine", Elsevier (Amsterdam, 1991).

In many of the synthetic schemes shown previously, $R^{12}$, $R^{13}$ and $R^{25-28}$ groups have been left off of the azocyclohexanes. However, it should be understood by the reader, that the azocyclohexanes can be fully substituted with these groups around the ring as stipulated by the scope of this application. In addition, many of the above synthetic schemes may be used in one form or another to generate the azocyclopentane and azocycloheptane starting materials needed to make the corresponding azocyclopentene and azocycloheptene compounds claimed in the scope of this application.

EXAMPLE 1

Preparation of 3-carboxy-4-[4-((4-Chloro-5-formyl-2-n-propylimidazol-1-yl)methyl)phenyl]-1-diphenylacetyl-1,2,3,6-tetrahydropyridine.

Part A. Preparation of 1-bromo-4-(tetrahydropyran-2-yloxymethyl)benzene

4-Bromobenzylalcohol (50.00 g, 270 mmol, 1 eq), 3,4-dihydro-2H-pyran (26.98 mL, 300 mmol, 1.1 eq), phosphorous oxychloride (0.3 mL) and ethyl ether (300 mL) were mixed and stirred for 48 h at 25° C. The reaction was worked up by rinsing once with saturated aqueous sodium bicarbonate solution, once with water followed by once with brine. The organic layer was dried (MgSO$_4$) and the solvent removed in vacuo to yield 72.00 g of crude product. The product (20.00 g) was flash chromatographed in 95:5 hexanes/ethyl acetate to yield 18.92 g of a colorless oil. NMR (CDCl$_3$) δ7.46 (d, 2H, J=9 Hz); 7.24 (d, 2H, J=9 Hz); 4.73 (d, 1H, J=12 Hz); 4.68 (m, 1H); 4.44 (d, 1H, J=12 Hz); 3.88 (m, 1H); 3.54 (m, 1H); 1.92–1.48 (m, 6H).

Part B. Preparation of 1-(tetrahydropyran-2-yloxymethyl)-4-(trimethyl stannyl) benzene.

A THF solution (75 mL) of the compound in Part A (5.00 g, 18.5 mmol, 1 eq) was added to a flame-dried flask containing freshly ground magnesium turnings (0.90 g, 36.9 nmmol, 2 eq) maintaining the temperature under 35° C. After 45 minutes, a precipitate began to form so that more THF was added to solublize the mixture. In a seperate flask, trimethyltin chloride (4.40 g, 22.1 mmol, 1.2 eq) was dissolved in THF and to it the solution of Grignard reagent was transferred at 0° C. via syringe with a slight exotherm being observed. The following day, the contents of the reaction were poured into a 5% ammonium chloride aqueous solution. The layers were separated, and the aqueous layer extracted with methylene chloride (2 X). The organic layers were combined, dried with (MgSO$_4$) and the solvent removed in vacuo to yield 6.52 g of an oil. Flash chromatography yielded 4.4 g of an oil. NMR (CDCl$_3$) δ7.48 (d, 2H, J=9 Hz); 7.35 (d, 2H, J=9 Hz); 4.77 (d, 1H, J=12 Hz); 4.72 (t, 1H, J=2 Hz); 4.48 (d, 1H, J=12 Hz); 3.92 (m, 1H); 3.54 (m, 1H); 1.94–1.47 (m, 6H); 0.27 (T, 9H, J=24 Hz).

Part C. Preparation of 1-t-butyloxycarbonyl-3-carbomethoxy-4-piperidone.

Methyl 4-piperidone-3-carboxylate hydrochloride (25.09 g, 130 mmol, 1 eq) was dissolved in methanol. Triethylamine (18.10 mL, 130 mmol, 1 eq) was added followed by di-t-butyldicarbonate (28.28 g, 130 mmol, 1 eq) all at 0° C. (Note: rapid CO$_2$ evolution). The mixture was stirred overnight at room temperature. The solvent was removed in vacuo. The residue was dissolved in ethyl acetate, and washed with 10% citric acid (3 X) and once with brine. The organic layer was dried (MgSO$_4$) and the solvent removed in vacuo to yield 24.62 g of an amber oil. NMR (CDCl$_3$) δ811.97 (s, 1H); 4.05 (m, 2H); 3.78 (s, 3H); 3.57 (t, 2H, J=7 Hz); 2.38 (bt, 2H, J=7 Hz); 1.47 (s, 9H).

Part D. Preparation of 1-t-butyloxycarbonyl-5-carbomethoxy-4-trifluoromethylsulfonyloxy-1,2,3,6-tetrahydropyridine.

The product in part C (24.62 g, 96 mmol, 1 eq) was dissolved in ethyl ether and added to sodium hydride (50% oil dispersion, 5.05 g, 105 mmol, 1.1 eq) previously washed with hexanes. The mixture was cooled to 0° C., and triflic anhydride (16.1 mL, 96 mmol, 1 eq) was added thereto dropwise. The reaction mixture was stirred for 3 h at 0° C. and was then allowed to warm to room temperature overnight. The mixture was worked up by pouring into water and extracting with ethyl acetate (3 X), combining the organic layers, drying (MgSO$_4$) and removing the solvent in vacuo to yield 32.23 g of a light yellow oil. Flash chromatography in 100% toluene to 9:1 toluene/ethyl acetate yielded 8.94 g of pure product as an oil. NMR (CDCl$_3$) δ4.28 (bs, 2H); 3.83 (s, 3H); 3.63 (m, 2H); 2.52 (m, 2H); 1.49 (s, 9H).

Part D. Preparation of 1-t-butyloxycarbonyl-5-carbomethoxy-4-(4-(tetrahydropyran-2yloxymethyl)-phenyl)-1,2,3,6-tetrahydropyridine.

The product of part B (a batch that was only 83% pure by NMR)(2.41 g, 5.63 mmol, 1.04 eq), the product of part D (1.63 g, 5.41 mmol, 1 eq), tetrakis (triphenylphosphine) palladium (0)( 130 mg, 0.108 mmol, 0.02 eq), lithium chloride (0.69 g, 16.2 mmol, 3 eq) and dioxane (50 mL) were mixed and refluxed overnight under nitrogen. The reaction was worked up by adding water and extracting with ethyl acetate (3X). The organic layers were combined, dried (MgSO$_4$), the solvent removed in vacuo and the residue flash chromatographed in 95:5 pentane/ethyl acetate to 75:25 pentane/ethyl acetate to yield 1.65 g of a colorless oil. NMR (CDCl$_3$) δ7.34 (d, 2H, J=8 Hz); 7.12 (d, 2H, J=8 Hz); 4.81 (d, 1H, J=11 Hz); 4.74 (m, 1H); 4.48 (d, 1H, J=11 Hz); 4.26 (bs, 2H); 4.00–3.80 (m, 1H); 3.70–3.50 (m, 3H); 3.50 (s, 3H); 2.49 (m, 2H); 2.00–11.40 (m, 6H); 1.50 (s, 9H).

Part E. Preparation of 1-t-butyloxycarbonyl-5-carbomethoxy-4-(4-(hydroxymethyl)phenyl)-1,2,3,6-tetrahydropyridine.

The product of part D (1.64 g, 3.8 mmol, 1 eq), p-toluenesulfonic acid monohydrate (72 mg, 0.38 mmol, 0.1 eq), and methanol (25 mL) were mixed and stirred for 0.5 h. The reaction was worked up by removing the solvent in vacuo, dissolving the residue in ethyl acetate and washing with saturated aqueous sodium bicarbonate (1 X) and with brine (1X). The organic layer was dried (MgSO$_4$), the solvent removed in vacuo to yield 1.20 g of a colrless oil. NMR (CDCl$_3$) δ7.34 (d, 2H, J=8 Hz); 7.14 (d, 2H, J=8 Hz); 4.70 (s, 2H); 4.26 (bs, 2H); 3.60 (t, 2H, J=7 Hz); 3.50 (s, 3H); 2.55–2.40 (m, 2H); 2.00–1.60 (m, 1H); 1.49 (s, 9H).

Part F. Preparation of 1-t-butoxycarbonyl-5-carbomethoxy-4-[4-((4-chloro-5-formyl-2-n-propylimidazol-1-yl)methyl)phenyl]-1,2,3,6-tetrahydropyridine.

The product of part E (1.20 g, 3.45 mmol, 1 eq) was dissolved in methylene chloride. Triethylamine (0.72 mL, 5.18 mmol, 1.5 eq) was added and the mixture was cooled to −78° C. Methanesulfonyl chloride (0.35 mL, 4.49 mmol, 1.3 eq) dissolved in methylene chloride was added dropwise. The reaction was allowed to warm to room temperature. After 3.5 h, the reaction was quenched by pouring into water and then extracting with methylene chloride (1X). The organic layer was washed with brine, dried (MgSO$_4$), and the solvent removed in vacuo to yield 1.46 g of the mesylate as an oil which was used immediately. The mesylate was dissolved in DMF. 4-Chloro-5-formyl-2-n-propylimidazole (0.77 g, 4.49 mmol, 1.3 eq) and potassium carbonate (0.95 g, 6.90 mmol, 2 eq) were then added and the mixture was stirred at room temperature overnight under nitrogen. The reaction was worked up by filtering off the potassium carbonate, and adding ethyl acetate. The organic layer was separated and washed with 1N NaOH (3X), brine (1X), dried (MgSO$_4$), the solvent removed in vacuo to yield 1.27 g of a yellow glass which was used without purification. NMR (CDCl$_3$) δ9.76 (s, 1H); 7.08 (d, 2H, J=8 Hz); 7.04 (d, 2H, J=8 Hz); 5.57 (s, 2H); 4.25 (bs, 2H); 3.60 (t, 2H, J=7 Hz); 3.55–3.40 (m, 3H); 2.63 (t, 2H, J=7 Hz); 2.47 (bs, 2H); 1.74 (t of q, 2H, J=7,7 Hz); 1.49 (s, 9 Hz); 0.95 (t, 3H, J=7 Hz).

Part G. Preparation of 5-carbomethoxy-4-[4-((4-chloro-5-formyl-2-n-propylimidazol)methyl)phenyl-1-yl]-1,2,3,6-tetrahydropyridine.

The product in part F (590 mg), trifluoroacetic acid (10 mL), anisole (2 mL), water (2 mL) and THF (10 mL) were mixed and stirred at 0° C. and allowed to warm to room temperature. After 24 h, more water (2 mL), anisole (2 mL), and trifluoroacetic acid (10 mL) were added at 0° C. and allowed to warm to room temperature. After 4 h, the reaction was worked up by adjusting the pH to 9–10 with 10N NaOH. The mixture was extracted with ethyl acetate (3X). The organic layers were combined, dried (MgSO$_4$), and the solvent removed in vacuo to yield 480 mg of a yellow glass. NMR shows some anisole present. The product was used without further purification in the next step. NMR (CDCl$_3$) δ9.76 (s, 1H); 7.10 (d, 2H, J=8 Hz); 7.02 (d, 2H, J=8 Hz); 5.55 (s, 2H); 3.74 (bs, 2H); 3.44 (s, 3H); 3.11 (t, 2H, J=7 Hz); 2.61 (t, 2H, J=7 Hz); 2.43 (bs, 2H); 1.75 (t of q, 2H, J=7,7 Hz); 0.95 (t, 3H, J=7 Hz).

Part H. Preparation of 5-carbomethoxy-4-[4-((4-chloro-5-formyl-2-n-propylimidazol-1-yl)methyl)phenyl]-1-diphenylacetyl-1,2,3,6-tetrahydropyridine.

The product in part G (470 mg, 1.17 mmol, 1 eq) was dissolved in THF. Huenig's base (0.20 mL, 1.17 mmol, 1 eq) was added and the mixture cooled to 0° C. Diphenylacetyl chloride (270 mg, 1.17 mmol, 1 eq) dissolved in THF, was added dropwise. After the addition was complete, the mixture was allowed to warm to room temperature. After 2 h, the reaction was worked up by removing the solvent in vacuo and adding water and ethyl acetate. The layers were separated. The organic layer was rinsed with water (2X). The organic layer was dried (MgSO$_4$), and the solvent removed in vacuo to yield 580 mg of a yellow glass. NMR shows amide bond rotamers. NMR (CDCl$_3$) δ9.75 (m, 1H); 7.41–7.10 (m, 10H); 7.10–6.80 (m, 4H); 5.60–5.45 (m, 2H); 5.33 (s, 0.5×1H); 5.26 (s, 0.5×1H); 4.49 (s, 0.5×1H); 4.29 (s. 0.5×1H); 3.83 (t, 0.5×2H, J=7 Hz); 3.62 (t, 0.5×2H, J=7 Hz); 3.49 (s, 0.5×3H); 3.45–3.30 (m, 0.5×3H); 2.62 (t, 2H, J=7 Hz); 2.49 (bs, 0.5×1H); 2.12 (bs, 0.5×1H); 1.74 (t pf q, 2H, J=7,7 Hz); 0.95 (t, 3H, J=7 Hz).

Part I. Preparation of 3-carboxy-4-[4-((4-Chloro-5-formyl-2-n-propylimidazol-1-yl)methyl)phenyl]-1-diphenylacetyl-1,2,3,6-tetrahydropyridine.

The product of part H (580 mg, 0.97 mmol, 1 eq), 1.000N NaOH (3.89 mL, 3.89 mmol, 4 eq), and THF (15 mL) were mixed and stirred at room temperature overnight. The mixture was worked up by adding water and removing the THF in vacuo. The pH was adjusted to 5-6 with 1N HCl. Solids precipitated. These were dissolved in chloroform and filtered through fiberglass filter paper to remove insoluble material. The filtrate was dried (MgSO$_4$), and the solvent removed in vacuo to yield 500 mg of yellow solids. Flash chromatography in 95:5 ethyl acetate/isopropanol to 100% isopropanol yielded 250 mg of a tan glass. MS (NH4+) detects M+H=582. Anal. calcd. for C$_{34}$H$_{32}$ClN$_3$O$_4$.(EtOAc)$_2$: C, 66.52; Cl, 4.68; N, 5.54. Found: C, 66.58; Cl, 4.59; N, 5.65. NMR shows that the double bond has migrated.

EXAMPLE 2

Preparation of 1-diphenylacetyl-4-[4-((5,7-dimethyl-2-ethyimidazopyridin-3-yl)methyl)phenyl-1-yl]-3-(tetrazol-5-yl)-1,2,3,6-tetrahydropyridine.

Part A. Preparation of N-Diphenylacetyl-4-piperidone

To a mixture of 4-piperidone.HCl monohydrate (10.00 g, 65 mmol, 1 eq) in 1.000N NaOH (65.00 mL, 65 mmol, 1 eq) and THF(250 mL) at 0° C. was added diphenylacetyl chloride (15.02 g, 65 mmol, 1.00 eq) dissolved in THF (50 mL) in 5 equal portions alternating with 5 equal portions of 1.000N NaOH keeping the temperature below 5° C. After 3 h, the reaction was worked up by adding ethyl acetate and separating the layers. The aqueous layer was extracted twice more with ethyl acetate. The organic layers were dried (MgSO$_4$), and the solvent removed in vacuo to yield 20.01 g of a yellow solid. Recrystallization from hot ethyl acetate (100 mL) yielded two crops: 12.04 g (m.p.=135°-136° C.) and 3.30 g (m.p.=129°-131° C.); NMR (CDCl$_3$) δ7.40-7.10 (m, 10H); 5.30 (s, 1H); 3.94 (t, 2H, J=7 Hz); 3.76 (t, 2H, J=7 Hz); 2.45 (t, 2H, J=7 Hz); 2.03 (t, 2H, J=7 Hz).

Part B. Preparation of N-Diphenylacetyl-4-piperidone-3-carboxaldehyde.

The product from part A (14.30 g, 48.76 mmol, 1 eq) was dissolved in a minimum of toluene and added dropwise to a solution of toluene (15 mL), ethyl formate (11.90 mL, 14.59 mmol, 3 eq) and sodium methoxide (2.87 g, 53.62 mmol, 1.1 eq) and the contents were stirred at 5° C. under N$_2$. After 24 h, water was added and the layers were separated. The organic layer was rinsed with water, followed by 5% NaOH. The aqueous phases were combined, acidified to pH=3 with 1N HCl. The mixture was extracted with ethyl acetate (3X). The ethyl acetate layers were combined, dried (MgSO$_4$) and the solvent removed in vacuo to yield 6.26 g of an amber glass. MS detects M+H=322. The product was used without further purification in the next step.

Part C. Preparation of N-diphenylacetyl-[2,3]-(isoxazol-[4,5]-yl)piperidine

The product from part B (5.63 g, 17.5 mmol, 1 eq), hydroxylamine.HCl (1.69 g, 24.5 mmol, 1.4 eq) and glacial acetic acid (50 mL) were mixed and refluxed for 1 h. The solvent was removed in vacuo and water was added. The mixture was extracted with ethyl acetate (3X). The organic layers were combined, dried (MgSO$_4$) and the solvent was removed in vacuo to yield 5.02 g of an amber glass. MS detects M+H=319. The product was used without further purification in the next step.

Part D. Preparation of N-Diphenylacetyl-4-piperidone-3-carbonitrile

The product from part C (5.02 g, 16.0 mmol, 1 eq) was dissolved in ethanol (50 mL) containing sodium (0.43 g, 18.9 mmol, 1.2 mmol) and the mixture was refluxed for 2 h. The ethanol was removed in vacuo and water was added. The pH was adjusted to 3 with 1N HCl. A little methanol was added to solublize the product. The mixture was extracted with ethyl acetate (3X). The organic layers were combined, dried (MgSO$_4$) and the solvent removed in vacuo to yield 4.54 g of an amber glass. Flash chromatography in 1:1 hexanes-/ethyl acetate yielded 2.31 g of a light yellow glass. IR (neat) 3062, 3029, 2252, 2208, 1732, 1643, 911 cm−1. NMR (DMSO-d$_6$) δ7.40-7.10 (m, 10H); 5.70-5.50 (m, 1H); 4.15-3.90 (m, 2H); 3.70-3.50 (m, 2H); 2.32-2.10 (m, 1H); 2.00-1.85 (m, 1H).

Part E. Preparation of 1-diphenylacetyl-5-cyano-4-(4-hydroxymethyl)phenyl)-1,2,3,6-tetrahydropyridine.

By using the coupling procedures described in example 1, the product from part D was converted into 1-diphenylacetyl-5-cyano-4-( 4-hydroxymethyl)phenyl)-1,2,3,6-tetrahydropyridine. IR (neat) 2245, 2214 cm−1. NMR (CDCl$_3$) δ7.50-7.20 (m, 14 H); 5.26 (s, 2H); 4.80-4.65 (m, 2H); 4.46 (s, 1H); 4.21 (s, 1H); 3.87 (t, 1H, J=7 HZ); 3.68 (t, 1H, J=7 Hz); 2.64 (m, 1H); 2.25 (m, 1H); 1.95-1.80 (m, 1H).

Part F. Preparation of 1-diphenylacetyl-5-(N-triphenylmethyltetrazol-5-yl)-4-(4hydroxymethyl)phenyl)-1,2,3,6-tetrahydropyridine.

The product in part E (1.64 g, 4.01 mmol, 1 eq), trimethyltin azide (1.03 g, 5.22 mmol, 1.3 eq) and xylenes (25 mL) were mixed and refluxed overnight. After 24 h, another 0.5 eq of trimethyltin azide was added and the mixture refluxed again overnight. The mixture was worked up by filtering the solid product and rinsing the solids with xylene. Drying yielded 1.66 g of the corresponding trimethyltin-tetrazole adduct. This material (entire batch, 2.70 mmol, 1 eq) was suspended in methylene chloride and THF and to it was added 10N NaOH (0.28 mL, 2.84 mmol, 1.05 eq). The mixture was stirred for 15 minutes at room temperature after which triphenylmethyl chloride (0.79 g, 2.84 mmol, 1.05 eq) was added and the cloudy reaction mixture eventually became clearer overnight. After 24 h, the solvent was removed in vacuo and the product flash chromatographed in 75:25 hexanes/ethyl acetate yielding 1.27 g of a white glass. NMR (CDCl$_3$) (major rotamer only) δ7.40-6.70 (m, 24H); 6.96 (d, 1H, J=8 Hz); 6.81 (d, 4H, J=8 Hz); 5.39 (s, 1H); 4.70 (s, 1H); 4.60-4.45 (3H, S); 3.92 (t, 2H, J=7 Hz); 2.58 (m, 2H); 1.60-1.35 (m, 1H).

Part G. Preparation of 1-diphenylacetyl-4-[4-((5,7-dimethyl-2-ethylimidazopyridin-3-yl)methyl)phenyl]-5-(N-triphenylmethyltetrazol-5-yl)-1,2,3,6-tetrahydropyridine.

The product from part F (1.25 g, 1.8 mmol, 1 eq) was added to a stirred solution of triethylamine (0.38 mL, 2.7 mmol, 1.5 eq) in methylene chloride. The mixture was cooled to −78° C., and methanesulfonylchloride (0.18 mL, 2.34 mmol, 1.3 eq) dissolved in methylene chloride (5 mL) was added dropwise. Once the addition was complete, the contents were allowed to warm to room temperature slowly over 2 h, after which the mixture was allowed to stir for another 1.5 h. The reaction contents were poured into water and extracted into methylene chloride. The methylene chloride layer was then rinsed with brine, dried (MgSO4) and the solvent removed in vacuo to yield 1.46 g of an amber oil which was used without further purification.

To a solution of 5,7-dimethyl-2-imidazopyridine (European Patent application number 400974,: May 30, 1990)(0.32 g, 1.8 mmol, 1 eq) in DMF (25 mL) was added NaH (50% dispersion in oil, 86 mg, 1.8 mmol, 1 eq) and the mixture was heated at 50° C. for 1 h. The mixture was cooled to 0° C. and a DMF solution of the mesylate from the preceding paragraph was added dropwise thereto. The reaction mixture was allowed to warm to room temperature.

After 24 h, the reaction contents were poured into water and extracted with methylene chloride (3X). The methylene chloride layers were combined, dried (MgSO4), the solvent removed in vacuo and the residue flash chromatographed in 1:1 hexane/ethyl acetate to 100% ethyl acetate to yield 890 mg of a white glass. NMR (major rotamer) (CDCl3) δ7.40-7.10 (m, 20 H); 7.00-6.70 (m, 10H); 5.40-5.20 (m, 3H); 4.50 (s, 2H); 3.90 (t, 2H, J=7 Hz); 2.80-2.45 (m, 9H); 2.22 (m, 1H); 1.35-1.15 (m, 3H).

Part H. Preparation of 1-diphenylacetyl-4-[4-((5,7-dimethyl-2-imidazopyridin-3-yl)methyl)phenyl]-5-(tetrazol-5-yl) -1,2,3,6-tetrahydropyridine.

The product from part G (890 mg) was dissolved in methanol (25 mL) and refluxed for 4 h after which the contents were stirred at room temperature overnight. Silica gel was added and the solvent removed in vacuo. The silica gel containing the product was quickly transferred to the top of a flash chromatography column and the compound was immediately chromatographed in 1:1 hexane/ethyl acetate followed by 9:1 chloroform/methanol to yield 600 mg of a white glass. The glass was dissolved in a minimum of ethyl acetate and triturated with ether followed by hexane. The solid material was filtered and dried to yield 287 mg (m.p 142° C.: slow decomposition). NMR (CDCl3) δ7.40-7.05 (m, 10H); 7.00-6.70 (m, 5H); 5.45-5.25 (m, 3H); 4.70-4.50 (m, 2H); 3.90 (t, 1H, J=7 Hz); 3.70 (t, 1H, J=7 Hz); 2.68 (m, 2H); 2.60-2.40 (m, 7H), 2.20 (m, 1H); 1.20-1.05 (m, 3H).

EXAMPLE 3

Preparation of 1-diphenylacetyl-4-[4-((5,7-dimethyl-2-imidazopyridin-3-yl)methyl)phenyl]-3-(n-butylsulfonamidoxarbonyl-1,2,3,6-tetrahydropyridine.

3-Carboxy-1-diphenylacety-4-[4-((2-ethyl-6,8-dimethylimidazopyridin-3yl)methyl)phenyl]-1,2,3,6-tetrahydropyridine was synthesized from 5,7-dimethyl-2-ethylimidazopyridine by the methods described in examples 1 and 2. This material (0.89 g, 1.52 mmol, 1 eq) together with N,N-carbonyldiimidazole (0.25 g, 1.52 mmol, 1 eq) was dissolved in THF (15 mL) and refluxed for 1.5 h. The reaction was cooled and n-butylsulfonamide (0.21 g, 1.52 mmol, 1 eq) together with 1,8-diazabicyclo[5.4.0.]undec-7-ene (DBU)(0.23 mL, 1.52 mmol, 1 eq) were added. The reaction was refluxed for 24 h after which the reaction was worked up by adding water and adjusting the pH to 4 with 1N HCl. This mixture was extracted with ethyl acetate (3X), the ethyl acetate layers combined, dried (MgSO4) and the solvent removed in vacuo to yield 1.12 g of a yellow glass. Flash chromatography in 100% ethyl acetate to 100% isopropanol yielded 430 mg of a white glass. FABMS detects M+H=704.

The compounds in Table 1 can be synthesized by methods disclosed in the synthesis of examples 1, 2, and 3 and by other methods familiar to one skilled in the art using the appropriate starting materials.

TABLE 1

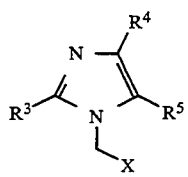

Category 1

| Ex. | R³ | R⁴ | R⁵ | X |
|---|---|---|---|---|
| 4 | n-propyl | Cl | CHO | 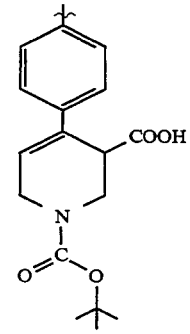 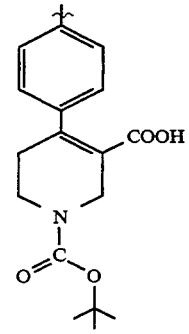<br>mixture (1) |

TABLE 1-continued
| 5 | n-propyl | Cl | COOH |
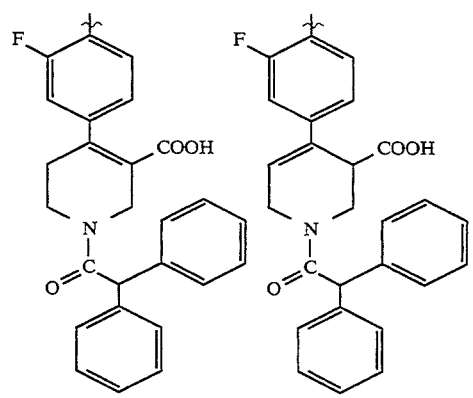
mixture
| 6 | n-propyl | ethyl | CHO |
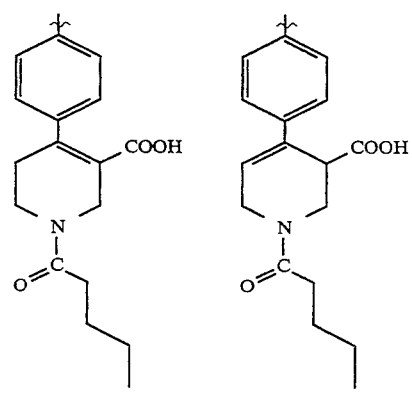
mixture (b)
| 7 | n-propyl | ethyl | CHO |
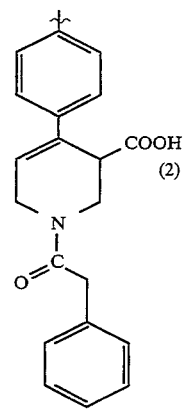
(2)

TABLE 1-continued
| | | | | |
|---|---|---|---|---|
| 8 | n-propyl | ethyl | CHO | 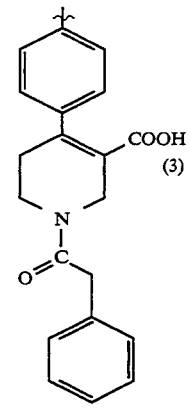 (3) |
| 9 | n-propyl | ethyl | CHO | 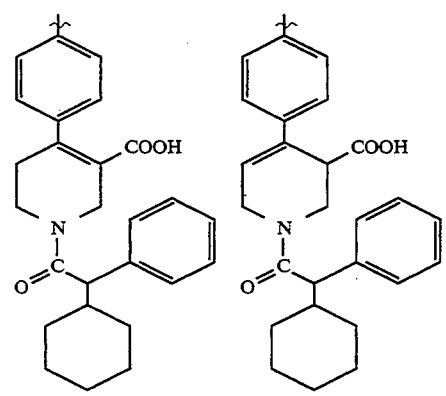 mixture (4) |
| 10 | n-propyl | ethyl | CHO | 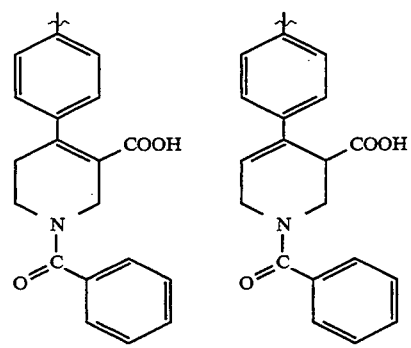 mixture (5) |
| 11 | n-propyl | ethyl | CHO | 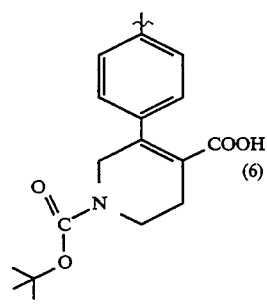 (6) |

TABLE 1-continued
| | | | | |
|---|---|---|---|---|
| 12 | n-propyl | ethyl | CHO | 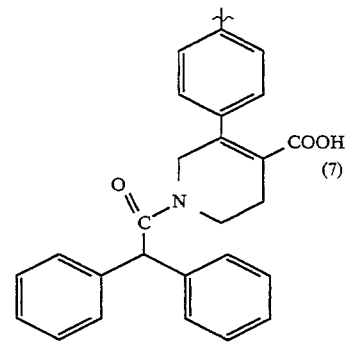 (7) |
| 13 | n-propyl | ethyl | COOH | 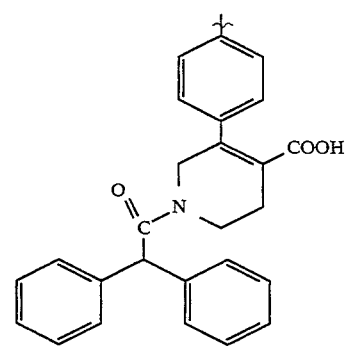 |
| 14 | CH$_3$CH=CH— | —SOCH$_3$ | COOH | 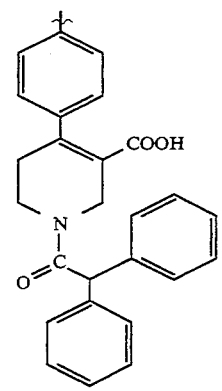 |
| 15 | CH$_3$CH$_2$C≡C— | —SO$_2$CH$_3$ | COOH | 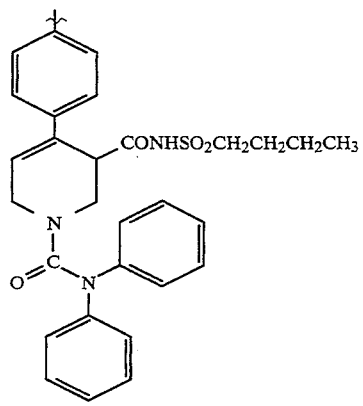 |

TABLE 1-continued
| 16 | n-propyl | ethyl | COOH |
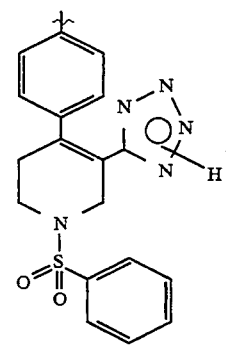
| 17 | n-propyl | ethyl | CN₄H |
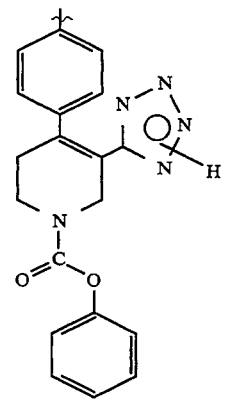
| 18 | n-propyl | ethyl | CONHOCH₃ |
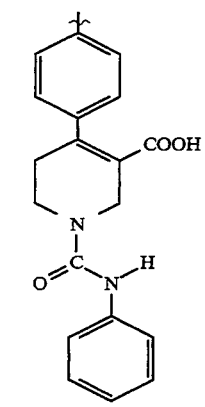
| 19 | CH₃CH=CH— | CF₂CF₃ | CONH(CH₃) |
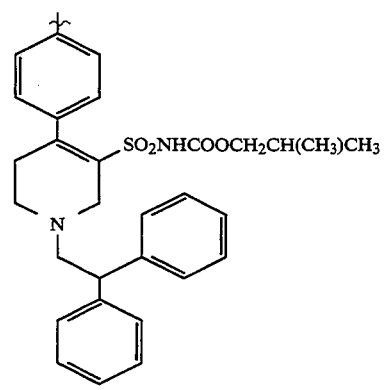

TABLE 1-continued
| | | | |
|---|---|---|---|
| 20 | n-butyl | Ph | COOH |
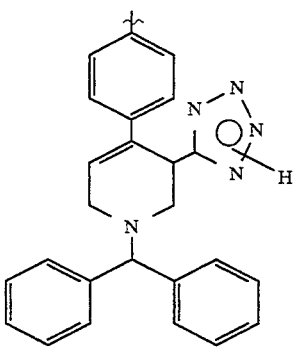
| | | | |
|---|---|---|---|
| 21 | n-butyl | Ph | NHSO$_2$CF$_3$ |
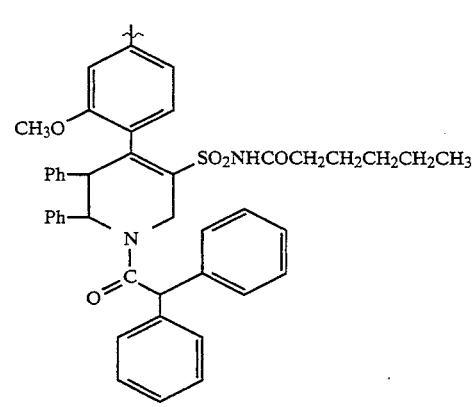
| | | | |
|---|---|---|---|
| 22 | Cl | CH$_2$OH | |
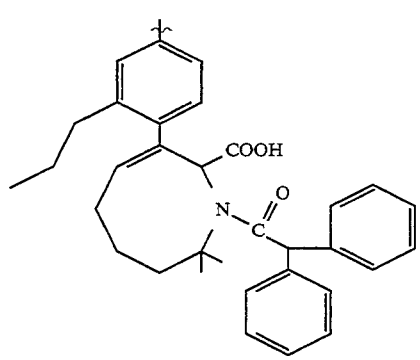
CH$_3$CH$_2$CH=CH—
| | | | |
|---|---|---|---|
| 23 | n-propyl | ethyl | COOH |
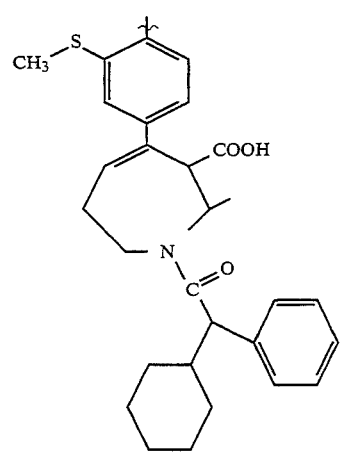

TABLE 1-continued
| | | | | |
|---|---|---|---|---|
| 24 | n-propyl | ethyl | COOH | 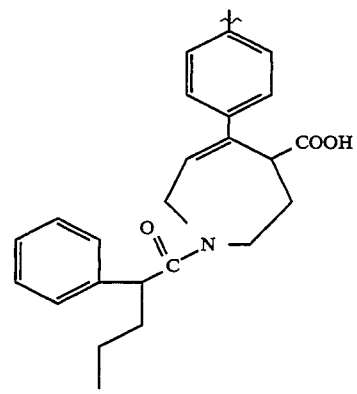 |
| 25 | n-propyl | ethyl | COOH | 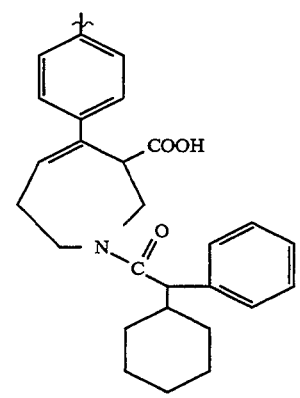 |
| 26 | n-propyl | ethyl | COOH | 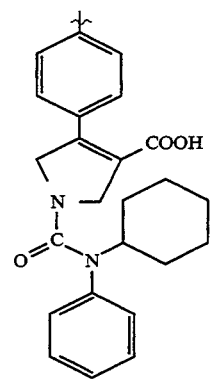 |
| 27 | n-butyl | Cl | COOH | 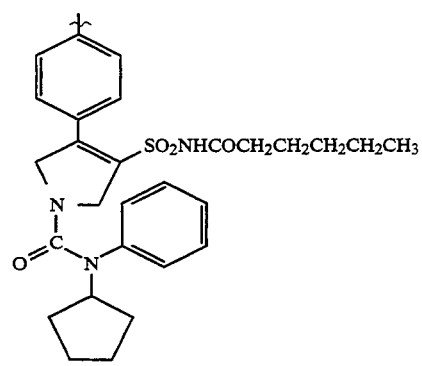 |

TABLE 1-continued

| 28 | n-butyl | CH₃ | COOH | |
| --- | --- | --- | --- | --- |
| 29 | n-propyl | Cl | COOH | |
| 30 | n-propyl | ethyl | CHO | |
| 31 | n-butyl | —SPh | COO(CH₂)₄Ph | |

TABLE 1-continued
| | | | | |
|---|---|---|---|---|
| 32 | n-pentyl | —SCH₃ | CHO | 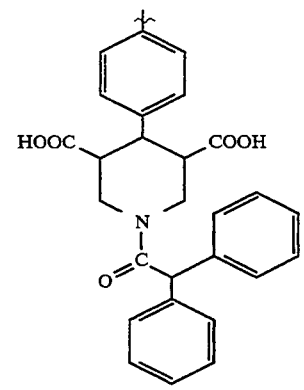 |
| | Category 2 | | |
|---|---|---|---|
| Ex | $R^3$ | $R^4 + R^5$ | X |
| 33 | ethyl | —C(CH₃)=CH—C(CH₃)=N— | 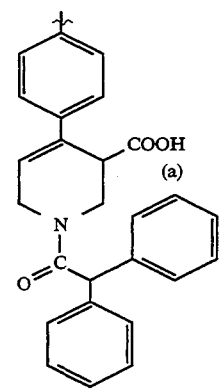 (a) |
| 34 | propyl | —C(CH₃)=CH—C(CH₃)=N— | 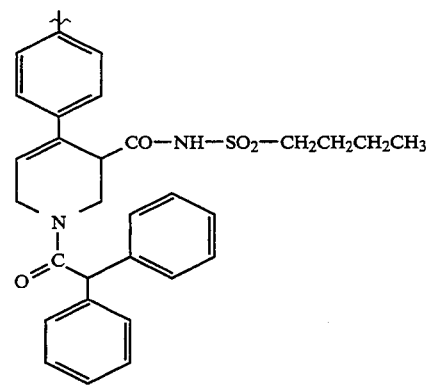 |
| 35 | ethyl | —C(CH₃)=CH—C(CH₃)=N— | 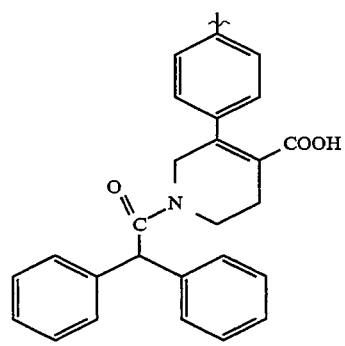 |

TABLE 1-continued
| 36 | ethyl | —C(CH₃)=CH—C(CH₃)=N— | 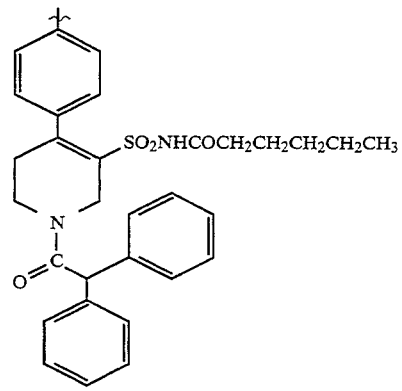 |
| 37 | ethyl | —C(CH₃)=CH—C(CH₃)=N— | 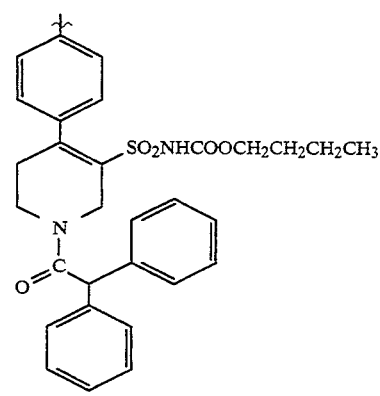 |
| 38 | ethyl | —C(CH₃)=CH—C(CH₃)=N— | 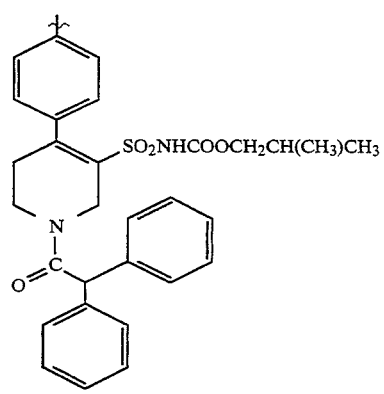 |
| 39 | n-propyl | —C(CH₃)=CH—C(CH₃)=N— | 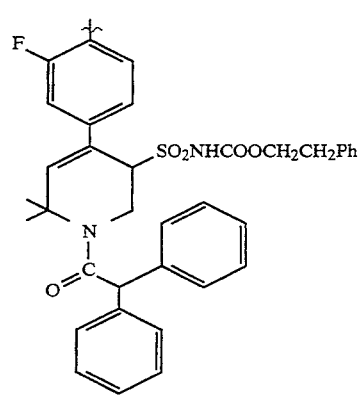 |

TABLE 1-continued
| 40 | ethyl | —C(CH₃)=CH—C(CH₃)=N— | 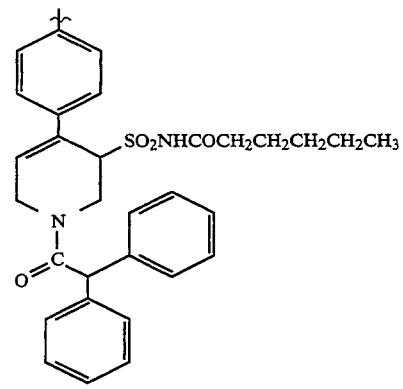 |
| 41 | ethyl | —C(CH₃)=CH—C(CH₃)=N— | 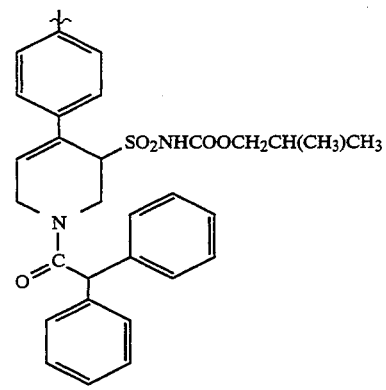 |
| 42 | ethyl | —C(CH₃)=CH—C(CH₃)=N— | 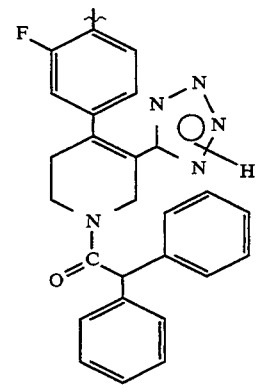 |
| 43 | ethyl | —C(CH₃)=CH—C(CH₃)=N— | 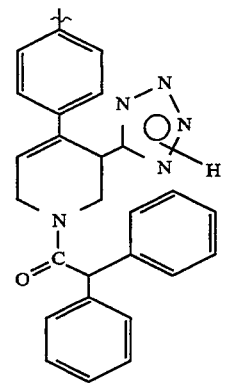 |

TABLE 1-continued
| | | | |
|---|---|---|---|
| 44 | ethyl | —C(CH₃)=CH—C(CH₃)=N— | 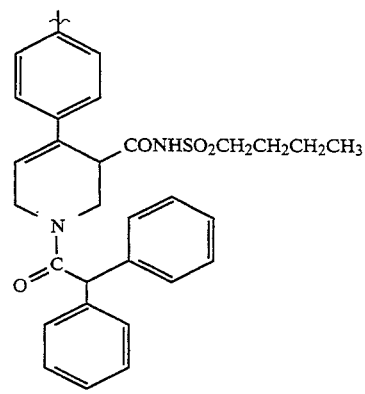 |
| 45 | ethyl | —C(CH₃)=CH—C(CH₃)=N— | 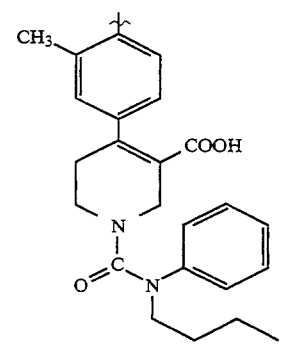 |
| 46 | ethyl | —C(CH₃)=CH—C(CH₂CH₃)=N— | 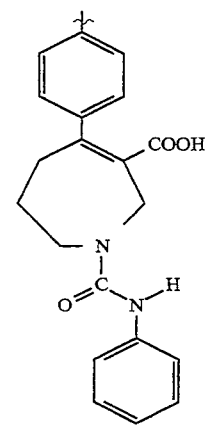 |
| 47 | n-propyl | —C(CH₃)=CH—CH=N— | 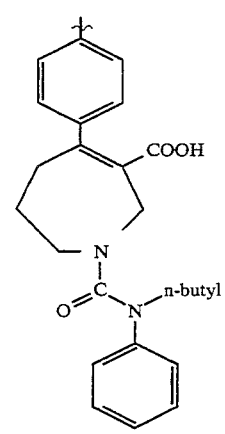 |

TABLE 1-continued
| 48 | ethyl | —(Ph)C=CH—C(CH₃)=N— | 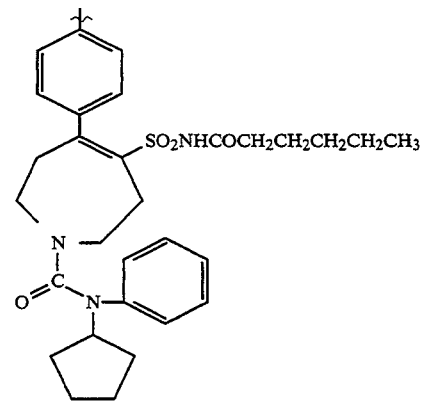 |
| 49 | ethyl | —(CH₃)C=CH—((CH₃)₂N)C=N— | 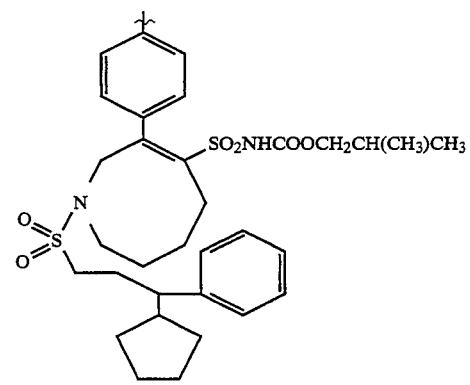 |
| 50 | ethyl | —(CH₃)C=CH—C(COOH)=N— | 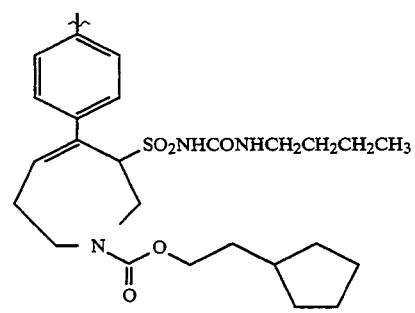 |
| 51 | ethyl | —(CH₃)C=CH—C(COOMe)=N— | 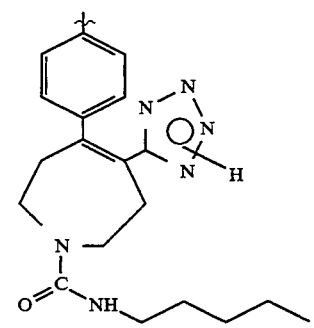 |

TABLE 1-continued
| 52 | ethyl | —(N(CH$_3$)$_2$)C=CHC(CONHSO$_2$(CH$_2$)$_3$CH$_3$)=N— | 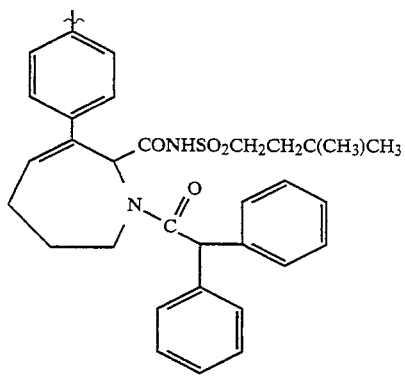 |
| 53 | ethyl | —C(CH$_3$))=CH—C(CN$_4$H)=N— | 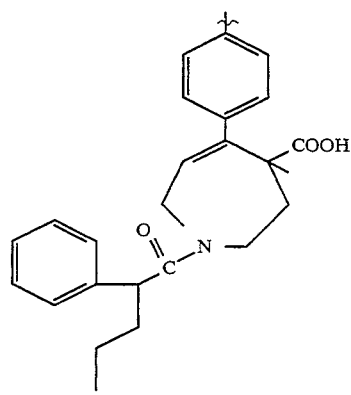 |
| 54 | ethyl | —(CH$_3$)C=CH—C(CH$_3$)=N— | 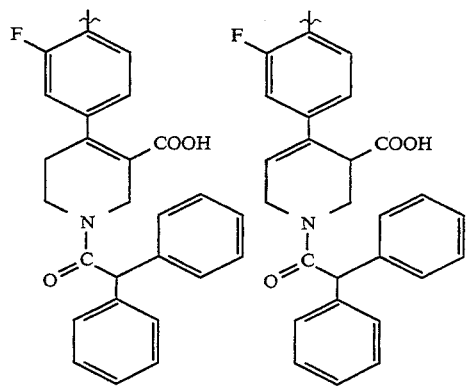 mixture |
| 55 | ethyl | —(CH$_3$)C=CH—C(CH$_3$)=N— | 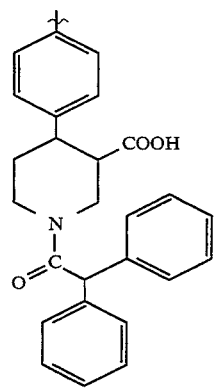 |

TABLE 1-continued

| | | | |
|---|---|---|---|
| 56 | ethyl | —(CH₃)C=CH—C(CH₃)=N— | 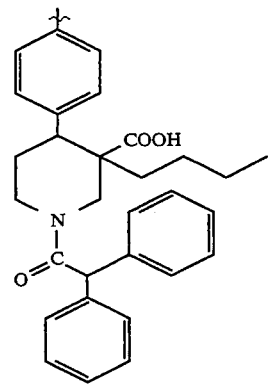 |
| 57 | ethyl | —(CH₃)C=CH—C(CH₃)=N— | 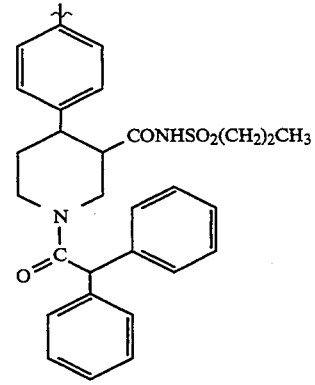 |

(1) MS m/e + H = 488
(2) MS m/e + H = 500
(3) MS m/e + H = 500
(4) MS m/e + H = 582
(5) MS m/e + H = 486
(6) MS m/e + H = 482
(7) MS m/e + H = 576

$^a$Analysis calculated for $C_{37}H_{36}N_4O_3 \cdot (H_2O)_{0.7}$: C, 74.40; H, 6.31; N, 9.38. Found: C, 74.49; H, 6.13; N, 9.23
$^b$Analysis calculated for $C_{27}H_{35}N_3O_4 \cdot (H_2O)_{0.3}$: C, 68.85; H, 7.62; N, 8.92. Found: C, 68.87; H, 7.50; N, 8.75.

Utility

Angiotensin-II (AII) produces numerous biological responses (e.g. vasoconstriction) through stimulation of its receptors on cell membranes. For the purpose of identifying compounds such as AII antagonists which are capable of interacting with AII receptors, a ligand-receptor binding assay was utilized.

DuP 753 and PD123177 were used as standards, and to block angiotensin II binding to the $AT_1$ and $AT_2$ sites, respectively. DuP 753 was synthesized according to the procedures described by Carini and Duncia (U.S. Pat. No. 5,138,069). PD123177 was prepared using the methods described by Blankely et al. (U.S. Pat. No. 4,812,462).

$AT_1$ site binding was determined in a rat adrenal cortical microsome preparation or in a rat liver membrane preparation. Results for $AT_1$ binding were similar in both assays. $AT_2$ site binding was determined using a rat adrenal medulla preparation. For the adrenal cortical microsome and adrenal medulla preparations, the method of Chiu, et al. (Receptor, 1, 33, 1990) was employed. For the liver membrane preparation, the method of Bauer et al. (Molecular Pharmacology, 39, 579–585, 1991) was used, with the following changes: male Charles River CD rats were employed; the homogenation buffer consisted of a solution of Trizma base (10 mM) and EDTA (5.0 mM) adjusted to pH 7.5 with 1N HCl; the binding buffer consisted of a solution of Trizma base (50 mM) and $MgCl_2 6H_2O$ (5 mM) adjusted to pH 7.20 with 6N HCl; and the binding was assessed using a 96 well plate format at 22° C. To illustrate the adrenal cortex assay, in brief, aliquots of a freshly prepared particulate fraction of rat adrenal cortex were incubated with 0.15 nM [$^{125}$I] AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by gamma counting. The inhibitory concentration ($IC_{50}$) of potential AII antagonists which gives 50% displacement of the total specifically bound [$^{125}$I] AII is presented as a measure of the affinity of such compound for the AII receptor. $AT_1$ site binding was determined in the presence of $10^{-6}$M PD123177. $AT_2$ site binding was determined in the presence of $10^{-6}$M DuP 753. $IC_{50}$ was determined by displacement of [$^{125}$I] AII from the receptor by the test compound.

Using the assay method described above, the compounds of this invention are found to exhibit an activity of at least $IC_{50} < 10$ micromolar at both the $AT_1$ and $AT_2$ receptors, thereby demonstrating and confirming the activity of these compounds as effective $AT_1/AT_2$ AII receptor antagonists.

The potential antihypertensive effects of the compounds of this invention may be demonstrated by administering the compounds to awake rats made hypertensive by ligation of the left renal artery (Cangiano, et al., *J. Pharmacol. Exp. Ther.*, 208, 310, 1979). This procedure increases blood pressure by increasing renin production with consequent elevation of AII levels. Compounds are administered intravenously via cannula in the jugular vein to give a cumulative dose of 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of this invention are useful in treating hypertension, and for the treatment of hyperuricemia, primary and secondary hyperaldosteronism, psoriasis, cardiac disorders such as acute and chronic congestive heart failure, angina pectoris, myocardial infarction, systolic and diastolic dysfunction, cardiac myopathy, and cardiac hypertrophy and hyperplasia, esp. left ventricular hypertrophy; pulmonary disorders such as primary and secondary pulmonary hypertension; vascular disorders such as atherosclerosis, restenosis after vascular injury associated with e.g. angioplasty or bypass surgery, vascular hypertrophy and hyperplasia, atheroma and Raynaud's disease; cerebrovascular disorders such as migraine, and ischemic and hemorragic stroke; renal disorders such as renal vascular hypertension, proteinuria of primary renal disease, end stage renal disease and renal transplant therapy, glomerulonephritis, nephrotic syndrome, scleroderma and glomerular sclerosis, and for enhancing renal blood flow; CNS disorders such as impairment of cognitive function and memory loss, addiction, anxiety, bulimia, depression, epilepsy, pain, Parkinson's disease, psychosis, sleep disorders and tardive dyskinesia; ocular disorders such as macular degeneration and elevated intraocular pressure; gastrointestinal and bladder disorders; disorders associated with diabetes, such as diabetic angiopathy, nephropathy and retinopathy, and for delaying the onset of type II diabetes. The application of the compounds of this invention for these and similar disorders will be apparent to those skilled in the art. The compounds of this invention are also useful as diagnostic agents, to test the renin angiotensin system.

Patients in need of treatment for elevated intraocular pressure can be treated with compounds of this invention administered in the form of typical pharmaceutical formulations such as tablets, capsules, injectables and the like as well as topical ocular formulations in the form of solutions, ointments, inserts, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, beta-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

Administration of a compound of this invention with a NSAID can prevent renal failure which sometimes results from administration of a NSAID. The compounds of this invention can also be administered in combination with other antihypertensives and/or diuretics. Administration of a compound of this invention with a diuretic, either as a stepwise combined therapy (diuretic first) or as a physical mixture, enhances the antihypertensive effect of the compound.

For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; b-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; a-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazine hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly. To illustrate these combinations, one of the angiotensin-II antagonists of this invention effective clinically in the 5–500 milligrams per day range can be effectively combined at levels at the 1.0–500 milligrams per day range with the following compounds at the indicated per day dose range: hydrochlorothiazide (6-100 mg), chlorothiazide (125-500 mg), ethacrynic acid (5-200 mg), amiloride (5-20 mg), furosemide (5-80 mg), propranolol (10-480 mg), timolol maleate (1-20 mg), methyldopa (125-2000 mg), felodipine (1-20 mg), nifedipine (5-120 mg), nitrendipine (5-60 mg), and diltiazem (30-540 mg). In addition, triple drug combinations of hydrochlorothiazide (5-100 mg) plus amiloride (5-20 mg) plus angiotensin-II antagonists of this invention (1-500 mg) or hydrochlorothiazide (5-100 mg) plus timolol maleate (5-60 mg) plus an angiotensin-II antagonists of this invention (1-500 mg) or hydrochlorothiazide (5-200 mg) and nifedipine (5-60 mg) plus an angiotensin-II antagonist of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A compound of formula (I):

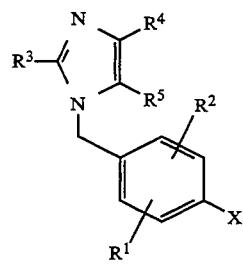

wherein
$R^1$ and $R^2$ are independently
  a) H,
  b) C1-C5-alkyl,
  c) —OH,
  d) C1-C4-alkoxy,
  e) —NO$_2$,
  f) —S(O)$_r$R$^{23}$, or
  g) Cl, F, Br;
$R^3$ is alkyl, alkenyl or alkynyl of 2-7 carbon atoms;
$R^4$ is
  a) H,
  b) Cl, Br, I,
  c) C1-C4-alkyl,
  d) C1-C4-perfluoroalkyl,
  e) phenyl or phenyl optionally substituted with halogen, C1-C4-alkyl, —OH or C1-C4-alkoxy, or
  f) —S(O)$_r$R$^{23}$;
$R^5$ is
  a) H,
  b) C1-C4 alkyl, c) —(CH$_2$)$_m$CHR$^{15}$OR$^{16}$,
d) —COR$^{17}$,
e) —(CH$_2$)$_m$CHR$^{15}$COR$^{17}$,
f) —CR$^{18}$=CR$^{19}$COR$^{17}$,
g) —CONHOR$^{20}$,
h) —(CH$_2$)$_m$OCOR$^{16}$,
i) —CH$_2$NHCOR$^{15}$,
j) —(CH$_2$)$_m$NHSO$_2$R$^{23}$,
l) tetrazol-5-yl, or
m) —CONHSO$_2$R$^9$;
R$^4$ and R$^5$ taken together to be

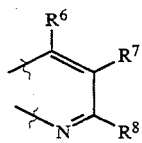

R$^6$, R$^7$, R$^8$ are independently
a) H,
b) C1-C4-alkyl, either unsubstituted or substituted with:
  i) —OH,
  ii) —CO$_2$R$^{32}$,
  iii) —NH$_2$,
  iv) (C1-C4-alkyl)amino,
  v) di(C1-C4-alkyl)amino,
c) halo,
d) —CF$_3$,
e) —OH,
f) —N(R$^{32}$)$_2$,
g) C1-C4-alkoxy,
h) —CO$_2$R$^{32}$,
i) —CONH$_2$,
j) —C3-C7-cycloalkyl,
k) aryl, wherein aryl is phenyl or napthyl optionally substituted with one or two substituents selected from the group consisting of F, Cl, Br, I, C1-C4-alkyl, C1-C4-alkoxy, —NO$_2$, —CF$_3$, C1-C4—S(O)$_r$—, —OH, —NH$_2$, —NH(C1-C4-alkyl), —N(C1-C4-alkyl)$_2$, —CO$_2$R$^{10}$;
l) heterocyclic, wherein heterocyclic is a five- or six-membered saturated or unsaturted ring containing 1-3 three heteroatoms selected from the group consisting of O, N or S wherein S may be in the form of sulfoxide or sulfone and which may be optionally substituted with one or two substituents which are members selected from the group consisting of F, Cl, Br, I, C1-C4-alkyl, C1-C4-alkoxy, —NO$_2$, —CF$_3$, C1-C4—S(O)$_r$—, —OH, —NH$_2$, —NH(C1-C4-alkyl), —N(C1-C4-alkyl)$_2$, —CO$_2$R$^{10}$;
m) —CONHSO$_2$R$^9$, or
n) tetrazol-5-yl;
R$^9$ is
a) C1-C4-alkyl,
b) phenyl or phenyl optionally substituted with halogen, C1-C4-alkyl, —OH or C1-C4-alkoxy;
R$^{10}$ is H, C1-C4-alkyl, or benzyl;
X is saturated or unsaturated

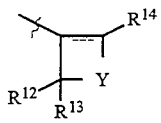 (a)

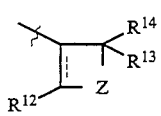 (b)

Y is
a) —NR$^{11}$(CR$^{25}$R$^{26}$)—,
b) —NR$^{11}$(CR$^{25}$R$^{26}$)(CR$^{27}$R$^{28}$)—,
c) —(CR$^{25}$R$^{26}$)NR$^{11}$(CR$^{27}$R$^{28}$)—,
d) —NR$^{11}$(CR$^{25}$R$^{26}$)(CR$^{27}$R$^{28}$)(CR$^{29}$R$^{30}$)—,
e) —(CR$^{25}$R$^{26}$)NR$^{11}$(CR$^{27}$R$^{28}$)(CR$^{29}$R$^{30}$)—,
f) —(CR$^{25}$R$^{26}$)(CR$^{27}$R$^{28}$)NR$^{11}$(CR$^{29}$R$^{30}$)—;
Z is
a) —(CR$^{25}$R$^{26}$)NR$^{11}$—,
b) —(CR$^{25}$R$^{26}$)(CR$^{27}$R$^{28}$)NR$^{11}$—,
c) —(CR$^{25}$R$^{26}$)NR$^{11}$(CR$^{27}$R$^{28}$)—,
d) —(CR$^{25}$R$^{26}$)(CR$^{27}$R$^{28}$)(CR$^{29}$R$^{30}$)NR$^{11}$—,
e) —(CR$^{25}$R$^{26}$)NR$^{11}$(CR$^{27}$R$^{28}$)(CR$^{29}$R$^{30}$)—,
f) —(CR$^{25}$R$^{26}$)(CR$^{27}$R$^{28}$)NR$^{11}$(CR$^{29}$R$^{30}$)—;
R$^{11}$ is
a) —COR$^{31}$,
b) —CO$_2$R$^{31}$,
c) —CONHR$^{31}$,
d) —CONR$^{31}$R$^{27}$,
e) —(CH$_2$)$_p$CHR$^{31}$R$^{27}$,
f) —SO$_2$R$^{31}$;
R$^{12}$, R$^{13}$ are independently
a) H,
b) alkyl of 1-7 carbon atoms, or
c) phenyl or phenyl optionally substituted with one or two substituents selected from the group consisting of F, Cl, Br, I, C1-C4-alkyl, C1-C4-alkoxy, —NO$_2$, —CF$_3$, C1-C4—S(O)$_r$—, —OH, —NH$_2$, —NH(C1-C4-alkyl), —N(C1-C4-alkyl)$_2$, —CO$_2$R$^{10}$;
R$^{14}$ is
a) —CO$_2$H,
b) —SO$_2$NHCO$_2$R$^{24}$,
c) —SO$_2$NHCOR$^{24}$,
d) —CONHSO$_2$R$^{24}$,
e) —SO$_2$NHCONHR$^{24}$,
f) —SO$_2$NHCSNHR$^{24}$, or

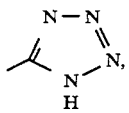

R$^{15}$ is
a) C$_1$-C$_4$-alkyl,
b) C$_3$-C$_6$-cycloalkyl,
c) aryl as defined above, or
d) —(C$_1$-C$_4$-alkyl)-aryl, —(C$_1$-C$_4$-alkyl)-aryl, where aryl is as defined above,
e) H;
R$^{16}$ is
a) H,
b) C$_1$-C$_6$-alkyl, c) —(CH$_2$)$_p$(aryl), where aryl is as defined above, or
d) —(CH$_2$)$_p$CH(diaryl), where aryl is as defined above;

R$^{17}$ is
a) H,
b) —OR$^{16}$,
c) —NR$^{21}$R$^{22}$;

R$^{18}$ and R$^{19}$ are independently
a) H,
b) C$_1$-C$_4$-alkyl,
c) aryl as defined above,
d) —CH$_2$ aryl, where aryl is as defined above;

R$^{20}$ is
a) H,
b) methyl,
c) benzyl;

R$^{21}$ and R$^{22}$ are independently
a) H,
b) C$_1$-C$_4$-alkyl,
c) aryl as defined above,
d) —CH$_2$aryl, where aryl is as defined above, or taken together comprise
e) —(CH$_2$)$_u$—, where u is 2 to 5,
f) a morpholine ring;

R$^{23}$ is
a) —CF$_3$,
b) C1-C6-alkyl,
c) phenyl;

R$^{24}$ is
a) aryl as defined above,
b) C3-C7-cycloalkyl
c) C1-C4-perfluoroalkyl,
d) C1-C10-alkyl optionally substituted with a substituent selected from the group consisting of:
  i) aryl as defined above,
  ii) heteroaryl, wherein heteroaryl is an unsubstituted, monosubstituted or disubstituted 5- or 6-membered aromatic ring which can optionally contain from 1 to 3 heteroatoms selected from the group consisting of O, N, and S and wherein the substituents are members selected from the group consisting of —OH, —SH, C$_1$-C$_4$-alkyl, C$_1$-C$_4$-alkoxy, —CF$_3$, halo, —NO$_2$, —CO$_2$R$^{10}$, —NH$_2$, C$_1$-C$_4$-alkylamino, C$_1$-C$_4$-dialkylamino,
  iii) —OH, —SH, C$_1$-C$_4$-alkyl, C$_1$-C$_4$-alkoxy, C$_1$-C$_4$-alkylthio, —CF$_3$, halo, —NO$_2$, —CO$_2$R$^{10}$, —NH$_2$, C$_1$-C$_4$-alkylamino, C$_1$-C$_4$-dialkylamino, —PO$_3$H$_2$;
e) heteroaryl as defined above;

R$^{25}$, R$^{26}$, R$^{27}$, R$^{28}$, R$^{29}$, R$^{30}$ are independently
a) H,
b) C1-C7-alkyl,
c) phenyl or phenyl optionally substituted with one or two substituents selected from the group consisting of F, Cl, Br, I, C1-C4-alkyl, C1-C4-alkoxy, —NO$_2$, —CF$_3$, C1-C4—S(O)$_n$, —OH, —NH$_2$, —NH(C1-C4-alkyl), —N(C1-C4-alkyl)$_2$, —CO$_2$R$^{10}$,
d) C3-C7-cycloalkyl;

R$^{31}$ is
a) —CH$_3$,
b) —CH$_2$CH$_3$,
c) —CH$_2$CH$_2$CH$_3$,
d) C4-C15-alkyl,
e) aryl as defined above,
f) —(C1-C10-alkyl)-aryl, where aryl is as defined above,
g) —(CH$_2$)$_p$CH(diaryl), where aryl is as defined above
h) C3-C7-cycloalkyl,
i) —C1-C5-alkyl-(C3-C7-cycloalkyl),
j) —(CH$_2$)$_p$CH(C3-C$_7$-cycloalkyl)(aryl), where aryl is as defined above,
k) —(CH$_2$)$_p$CH(C1-C6-alkyl)(aryl), where aryl is defined as above;

R$^{32}$ is
a) C1-C15 alkyl,
b) aryl defined as above, or
c) aryl(C1-C10)alkyl, where aryl is defined as above;

m is 0 to 2;
is 0 to 6;
r is 0 to 2;
u is 2 to 5;
and pharmaceutically acceptable salts thereof.

2. A compound of claim 1 wherein:
R$^1$ and R$^2$ are independently
a) H,
b) C1-C5-alkyl,
g) Cl, F, Br;

R$^3$ is alkyl or alkenyl of 2-7 carbon atoms;

R$^4$ is
a) Cl, Br, I,
b) C1-C4-alkyl,
c) C1-C4-perfluoroalkyl,
d) phenyl or phenyl optionally substituted with halogen, C1-C4-alkyl, —OH or C1-C4-alkoxy;

R$^5$ is
a) —(CH$_2$)$_m$CHR$^{15}$OR$^{16}$,
b) —COR$^{17}$,
c) —(CH$_2$)$_m$CHR$^{15}$COR$^{17}$,
d) —CR$^{18}$=CR$^{19}$COR$^{17}$,
e) —CONHOR$^{20}$,
f) —(CH$_2$)$_m$NHSO$_2$R$^{23}$,
g) —CONHSO$_2$R$^9$;

R$^6$, R$^7$, R$^8$ are independently
a) H,
b) C1-C4-alkyl
c) —CO$_2$R$^{32}$,
d) —CONHSO$_2$R$^9$, or
e) phenyl;

R$^{12}$, R$^{13}$ are independently
a) H,
b) C1-C7-alkyl, or
c) phenyl;

R$^{24}$ is
a) aryl as defined above,
b) C3-C7-cycloalkyl,
c) C1-C4-perfluoroalkyl,
d) C1-C10-alkyl optionally substituted with phenyl.

3. A compound of claim 2 wherein:
R$^5$ is
a) —CH$_2$OR$^{16}$,
b) —COR$^{17}$,
c) —CONHSO$_2$R$^9$;

R$^6$, R$^7$, R$^8$ are independently
a) H,
b) C1-C4-alkyl
c) —CO$_2$R$^{32}$,
d) —CONHSO$_2$R$^9$;

Y is
a) —NR$^{11}$(CR$^{25}$R$^{26}$)—, b) —NR$^{11}$(CR$^{25}$R$^{26}$)(CR$^{27}$R$^{28}$)—,
c) —(CR$^{25}$R$^{26}$)NR$^{11}$(CR$^{27}$R$^{28}$)—;

Z is
a) —(CR$^{25}$R$^{26}$)NR$^{11}$—,
b) —(CR$^{25}$R$^{26}$)(CR$^{27}$R$^{28}$)NR$^{11}$—,
c) —(CR$^{25}$R$^{26}$)NR$^{11}$(CR$^{27}$R$^{28}$)—.

4. A compound of claim 1 selected from the group consisting of:

1-Diphenylacetyl-4-[4-((5,7-dimethyl-2-ethylimidazopyridin-3-yl)methyl)phenyl]3-tetrazol-5-yl)-1,2,3,6,-tetrahydropyridine.

1-Diphenylacetyl-4-[4-((5,7-dimethyl-2-ethylimidazopyridin-3-yl)methyl)phenyl]3-(n-butylsulfonamidocarbonyl)-1,2,3,6,-tetrahydropyridine.

1-Diphenylacetyl-4-[4-((5,7-dimethyl-2-ethylimidazopyridin-3-yl)methyl)phenyl]3-carboxy-1,2,3,6,-tetrahydropyridine.

5. A pharmaceutical composition comprising a pharmaceutically suitable carrier and a compound of any one of claims 1 through 3 or 4.

6. A method of treating hypertension in a warm blooded animal comprising administering to an animal in need of such treatment an effective amount of a compound of any of claims 1 through 3 or 4.

7. A method of treating congestive heart failure in a warm blooded animal comprising administering to an animal in need of such treatment an effective amount of a compound of any of claims 1 through 3 or 4.

* * * * *